(12) United States Patent
Liu et al.

(10) Patent No.: US 7,582,611 B2
(45) Date of Patent: Sep. 1, 2009

(54) MOTILIDE COMPOUNDS

(75) Inventors: Yaoquan Liu, Castro Valley, CA (US); Christopher Carreras, Belmont, CA (US); David C. Myles, Kensington, CA (US); Yong Li, Palo Alto, CA (US); Simon James Shaw, San Francisco, CA (US); Hong Fu, Union City, CA (US); Yue Chen, Hayward, CA (US); Hao Zheng, Hayward, CA (US); Yandong Li, San Jose, CA (US); Mark A. Burlingame, Oakland, CA (US)

(73) Assignee: Pfizer Inc., New York, NY (US)

( * ) Notice: Subject to any disclaimer, the term of this patent is extended or adjusted under 35 U.S.C. 154(b) by 410 days.

(21) Appl. No.: 11/416,519

(22) Filed: May 2, 2006

(65) Prior Publication Data

US 2006/0270616 A1 Nov. 30, 2006

Related U.S. Application Data

(60) Provisional application No. 60/748,898, filed on Dec. 8, 2005, provisional application No. 60/715,406, filed on Sep. 8, 2005, provisional application No. 60/684,612, filed on May 24, 2005.

(51) Int. Cl.
  *A61K 31/70* (2006.01)
  *C07H 17/08* (2006.01)
(52) U.S. Cl. .......................... 514/29; 536/7.2; 536/7.3; 536/7.4
(58) Field of Classification Search ................. 536/7.2, 536/7.3, 7.4
See application file for complete search history.

(56) References Cited

U.S. PATENT DOCUMENTS

| | | | |
|---|---|---|---|
| 3,855,200 A | 12/1974 | Krowicki |
| 3,939,144 A | 2/1976 | Radobolja |
| 3,983,103 A | 9/1976 | Kobrehel |
| 4,588,712 A | 5/1986 | Toscano |
| 5,008,249 A | 4/1991 | Omura |
| 5,175,150 A | 12/1992 | Omura |
| 5,444,051 A | 8/1995 | Agouridas |
| 5,470,961 A | 11/1995 | Harada |
| 5,523,401 A | 6/1996 | Freiberg |
| 5,523,418 A | 6/1996 | Freiberg |
| 5,538,961 A | 7/1996 | Freiberg |
| 5,554,605 A | 9/1996 | Freiberg |
| 5,561,118 A | 10/1996 | Agouridas |
| 5,578,579 A | 11/1996 | Lartey |
| 5,654,411 A | 8/1997 | Lartey |
| 5,658,888 A | 8/1997 | Koga |
| 5,712,253 A | 1/1998 | Lartey |
| 5,770,579 A | 6/1998 | Agouridas |
| 5,834,438 A | 11/1998 | Lartey |
| 5,922,849 A | 7/1999 | Premchandran |
| 5,959,088 A | 9/1999 | Miura |
| 6,075,011 A | 6/2000 | Or et al. |
| 6,084,079 A | 7/2000 | Keyes |
| 6,169,168 B1 | 1/2001 | Asaka |
| 6,562,795 B2 | 5/2003 | Ashley |
| 6,750,205 B2 | 6/2004 | Ashley et al. |
| 6,875,576 B2 | 4/2005 | Carreras |
| 6,946,482 B2 | 9/2005 | Santi |
| 2002/0025936 A1 | 2/2002 | Ashley |
| 2002/0094962 A1 | 7/2002 | Ashley |
| 2002/0192709 A1 | 12/2002 | Carreras |
| 2004/0138150 A1 | 7/2004 | Santi |
| 2005/0113319 A1 | 5/2005 | Carreras |
| 2005/0119195 A1 | 6/2005 | Carreras |
| 2005/0256064 A1 | 11/2005 | Liu |

FOREIGN PATENT DOCUMENTS

| | | |
|---|---|---|
| DE | 2402200 | 1/1974 |
| GB | 1416281 | 12/1975 |
| GB | 1461032 | 1/1977 |
| JP | 60-218321 | 1/1985 |
| JP | 2002/241391 | 8/2002 |
| WO | WO 2006/070937 A1 | 7/2006 |

OTHER PUBLICATIONS

Bartner et al., *J. Chem. Soc., Perkin Trans. I* (1972-1999) 1979, (6), 1600-24, "The megalomicins. Part 7. A structural revision by carbon-13 nuclear magnetic resonance and x-ray crystallography. Synthesis and conformational analysis of 3-dimethylamino- and 3-azido-D- and -L-hexo-pyranosides, and the crystal structure of 4"-O-(4-iodobenzoyl)megalomicin A".

(Continued)

*Primary Examiner*—Elli Peselev
(74) *Attorney, Agent, or Firm*—Fitzpatrick, Cella, Harper & Scinto

(57) ABSTRACT

Compounds having a structure according to formula (I)

(I)

where $R^A$, $R^B$, $R^C$, $R^D$, $R^E$, and $R^F$ are as defined herein, are useful as prokinetic agents.

16 Claims, No Drawings

OTHER PUBLICATIONS

Bojarska-Dahlig et al., *Polish J. Pharmacology Pharmacy*, 1981 33 (3), 359-63, "Quantitative structure-activity relationships in erythromycin group with MTD technique".
Chemical Abstracts No. 104: 82047 (abstract of JP 60-218321).
Chemical Abstracts No. 137:185759 (abstract of JP 2002/241391).
Depoortere et al., *J. Gastrointestinal Motility*, 1, 150-159 (1989), "Structure-Activity Relation Erythromycin-Related Macrolides in Inducing Contractions and in Displacing Bound Motilin in Rabbin Duodenum".
Egan et al., *J. Antibiotics*, 1978, 31 (1), 55-62, "The structures of the m-chloroperbenzoic acid oxidation products of 8,9-anhydroerythromycins A- and B-6,9-hemiacetal and of (8S)-8-hydroxyerythromycin B".
Faghih et al., *Biorg. & Med. Chem. Lett.*, 1998, 8, 805-810, "Preparation of 9-Deoxo-4"-deoxy-6,9-epoxyerythromycin Lactams "Motilactides": Potent and Orally Active Prokinetic Agents.
Faghih et al., *J. Med. Chem.*, 1998, 41, 3402-3408, "Synthesis of 9-Deoxo-4"-deoxy-6,9-epoxyerythromycin Derivatives: Novel and Acid-stable Motilides".
Faghih et al., *Synlett.*, Jul. 1998, 751, "Entry into Erythromycin Lactams: Synthesis of Erythromycin A Lactam Enol Ether as a Potential Gastrointestinal Prokinetic Agent".
Hunt et al., *J. Antibiotics*, 1989, 42 (2), 293-298, "9,11-Cyclic Acetal Derivatives of (9S)-9-Dihydroerythromycin A".
Kobrehel et al., *Eur. J. Med. Chemistry*, 1978, 13 (1), 83-7, "Erythromycin series. VIII. Synthesis and biological activity of N-(substituted-benzenesulfonyl)erythromycins".
Krowicki et al., *J. Antibiotics* 1973 26 (10), 575-81, "Chemical modification of erythromycins. II. 8-Hydroxyerythromycin A".
Krowicki et al., *J. Antibiotics* 1974, 27 (8), 626-630, "Chemical modification of erythromycins. V. Cyclic carbonates of 8-hydroxyerythromycin A".
Lartey et al., *J. Med. Chem.*, 1995, 38, 1793-1798, "Synthesis of 4-"-Deoxy Motilides: Identification of a Potent and Orally Active Prokinetic Drug Candidate".
Massey et al., *J. Med. Chem.*, 1974, 17 (1), 105-107, "Antibacterial Activity of 9(S)-Erythromycylamine-Aldehyde Condensation Products".
Matijasevic et al., *Croatica Chemica Acta*, 1980, 53(3), 519-24, "Erythromycin series. X. Inhibitory activity of several new erythromycin derivatives in cell-free amino acid polymerization systems".
Myles et al., *J. Org. Chem.*, 1990, 55, 1636-1648, "Development of a Fully Synthetic Stereoselective Route to 6-Deoxyerythronolide B by Reiterative Applications of the Lewis Acid Catalyzed Diene Aldehyde Cyclocondensation Reaction: A Remarkable Instance of Diastereofacial Selectivity".
Naperty et al., *Roczniki Chemii*, 1977, 51 (6), 1207-10, "Erythromycin Derivatives. Part IX. Cyclic 8,9-carbonate of 8-hydroxyerythromycin B".
Omura et al., *J. Antibiotics* 1985, 38, 1631-2, "Gastrointestinal Motor-Stimulating Activity of Macrolide Antibiotics and the Structure-Activity Relationship".
Radobolja et al., *Croatica Chemica Acta*, 1985, 58 (2), 219-25, "Erythromycin Series. IX. Acid solvolysis of N-(4-substituted-benzensulfonyl)erythromycylamines".
Ryden et al., *J. Med. Chemistry*, 1973, 16 (9), 1059-1060, "N-Substituted Derivatives of Erythromycylamine".
Stanat et al., *Mol. Cell Biochem.*, 2003, 254, 1-7, "Characterization of the Inhibitory Effects of Erythromycin and Clarithromycin on the HERG Potassium Channel".
Yan et al., *Antimicrobial Agents and Chemotherapy* 2005, 49 (8), 3367-3372, "Fluorescence Polarization Method to Characterize Macrolide-Ribosome Interactions".

MOTILIDE COMPOUNDS

CROSS-REFERENCE TO RELATED APPLICATIONS

This application claims the benefit under 35 U.S.C. §119(e) of U.S. Provisional Applications Nos. 60/684,612, filed May 24, 2005; 60/715,406, filed Sep. 8, 2005; and 60/748,898, filed Dec. 8, 2005; the disclosures of which are incorporated herein by reference.

BACKGROUND OF THE INVENTION

1. Field of the Invention

This invention relates to agents for the treatment of gastrointestinal motility disorders and methods for their preparation and use.

2. Description of Related Art

Gastrointestinal ("GI") motility regulates the orderly movement of ingested material through the gut to ensure adequate absorption of nutrients, electrolytes, and fluids. Proper transit of the GI contents through the esophagus, stomach, small intestine, and colon depends on regional control of intraluminal pressure and several sphincters, which regulate their forward movement and prevent back-flow. The normal GI motility pattern may be impaired by a variety of circumstances, including disease and surgery.

GI motility disorders include gastroparesis and gastroesophageal reflux disease ("GERD"). Gastroparesis, whose symptoms include stomach upset, heartburn, nausea, and vomiting, is the delayed emptying of stomach contents. GERD refers to the varied clinical manifestations of the reflux of stomach and duodenal contents into the esophagus. The most common symptoms are heartburn and dysphasia, with blood loss from esophageal erosion also known to occur. Other examples of GI disorders in which impaired GI motility is implicated include anorexia, gall bladder stasis, postoperative paralytic ileus, scleroderma, intestinal pseudoobstruction, irritable bowel syndrome, gastritis, emesis, and chronic constipation (colonic inertia).

Motilin is a 22-amino acid peptide hormone secreted by endocrine cells in the intestinal mucosa. Its binding to the motilin receptor in the GI tract stimulates GI motility. The administration of therapeutic agents that act as motilin agonists ("prokinetic agents") has been proposed as a treatment for GI disorders.

The erythromycins are a family of macrolide antibiotics made by the fermentation of the Actinomycetes *Saccharopolyspora erythraea*. Erythromycin A, a commonly used antibiotic, is the most abundant and important member of the family. (In the erythromycins, the 16-member lactone ring is referred to as the macrolactone or aglycone portion of the molecule and the glycosidic residues pendant from the carbon at positions 3 and 5 are referred to as the cladinose and desosamine residues, respectively.)

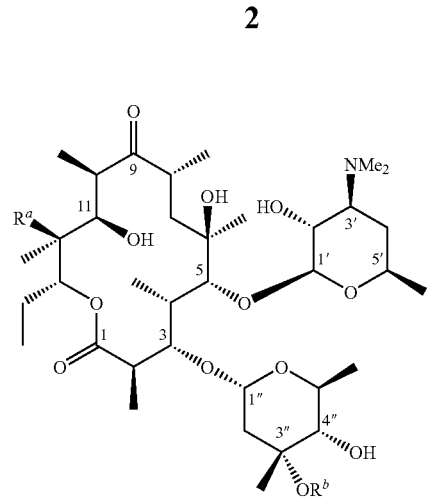

(1) Erythromycin A  $R^a$ = OH  $R^b$ = Me
(2) Erythromycin B  $R^a$ = H   $R^b$ = Me
(3) Erythromycin C  $R^a$ = OH  $R^b$ = H
(4) Erythromycin D  $R^a$ = H   $R^b$ = H The side effects of erythromycin A include nausea, vomiting, and abdominal discomfort. These effects have been traced to motilin agonist activity in erythromycin A (1) and, more so, its initial acid-catalyzed degradation product (5). (The secondary degradation product, spiroketal (6), is inactive.)

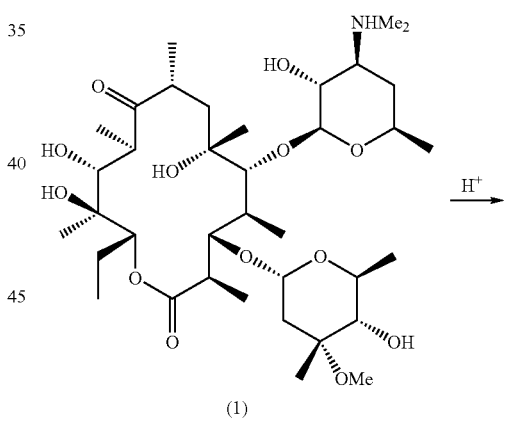

(1)

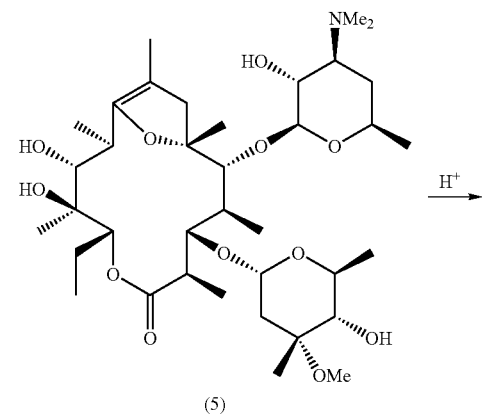

(5)

-continued

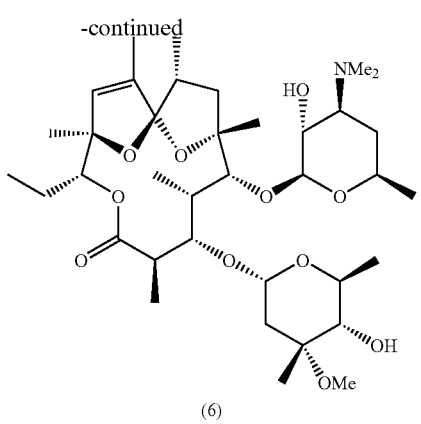

(6)

Spurred by the discovery of motilin agonist activity in erythromycin A and degradation product 5, researchers have endeavored to discover new motilides, as macrolides with prokinetic activity are called. Much of the research has centered on generating new erythromycin analogs, either via post-fermentation chemical transformation of a naturally produced erythromycin or via modification (including genetic engineering) of the fermentation process. Illustrative disclosures relating to motilides include: Omura et al., U.S. Pat. No. 5,008,249 (1991) and U.S. Pat. No. 5,175,150 (1992); Harada et al., U.S. Pat. No. 5,470,961 (1995); Freiberg et al., U.S. Pat. No. 5,523,401 (1996); U.S. Pat. No. 5,523,418 (1996); U.S. Pat. No. 5,538,961 (1996); and U.S. Pat. No. 5,554,605 (1996); Lartey et al., U.S. Pat. No. 5,578,579 (1996); U.S. Pat. No. 5,654,411 (1997); U.S. Pat. No. 5,712,253 (1998); and U.S. Pat. No. 5,834,438 (1998); Koga et al., U.S. Pat. No. 5,658,888 (1997); Miura et al., U.S. Pat. No. 5,959,088 (1998); Premchandran et al., U.S. Pat. No. 5,922,849 (1999); Keyes et al., U.S. Pat. No. 6,084,079 (2000); Ashley et al., US 2002/0025936 A1 (2002); Ashley et al., US 2002/0094962 A1 (2002); Carreras et al., US 2002/0192709 A1 (2002); Ito et al., JP 60-218321 (1985) (corresponding Chemical Abstracts abstract no. 104:82047); Santi et al., US 2004/138150 A1 (2004); Carreras et al., US 2005/0113319 A1 (2005); Carreras et al., US 2005/0119195 A1 (2005); Liu et al., US 2005/0256064 A1 (2005); Omura et al., *J. Antibiotics* 1985, 38, 1631-2; Faghih et al., *Biorg. & Med. Chem. Lett.*, 1998, 8, 805-810; Faghih et al., *J. Med. Chem.*, 1998, 41, 3402-3408; Faghih et al., *Synlett.*, July 1998, 751; and Lartey et al., *J. Med. Chem.*, 1995, 38, 1793-1798.

Also potentially pertinent to the present invention are erythromycin scaffold compounds having a derivatized ether oxygen or nitrogen at the 9-position, even where such compounds are not motilin agonists, illustrative disclosures being: Krowicki et al., U.S. Pat. No. 3,855,200 (1974); Radobolja et al., U.S. Pat. No. 3,939,144 (1976); Kobrehel et al., U.S. Pat. No. 3,983,103 (1976); Toscano, U.S. Pat. No. 4,588,712 (1986); Agouridas et al., U.S. Pat. No. 5,444,051 (1995); Agouridas et al., U.S. Pat. No. 5,561,118 (1996); Agouridas et al., U.S. Pat. No. 5,770,579 (1998); Asaka et al., U.S. Pat. No. 6,169,168 B1 (2001); Kobrehel et al., DE 2,402, 200 (1974); Pliva Pharmaceuticals, GB 1,416,281 (1975); Pliva Pharmaceuticals, GB 1,461,032 (1977); Asaga et al., JP 2002/241391 (2002); Ryden et al., *J. Med. Chemistry*, 1973, 16 (9), 1059-1060; Naperty et al., *Roczniki Chemii*, 1977, 51 (6), 1207-10; Kobrehel et al., *Eur. J. Med. Chemistry*, 1978, 13 (1), 83-7; Egan et al., *J. Antibiotics*, 1978, 31 (1), 55-62; Matijasevic et al., *Croatica Chemica Acta*, 1980, 53 (3), 519-24; Radobolja et al., *Croatica Chemica Acta*, 1985, 58 (2), 219-25; Hunt et al., *J. Antibiotics*, 1989, 42 (2), 293-298; Myles et al., *J. Org. Chem.*, 1990, 55, 1636-1648.

The disclosures of all of the foregoing documents are incorporated herein by reference.

BRIEF SUMMARY OF THE INVENTION

In a first aspect, this invention provides a compound, useful as a prokinetic agent, having a structure represented by formula (I)

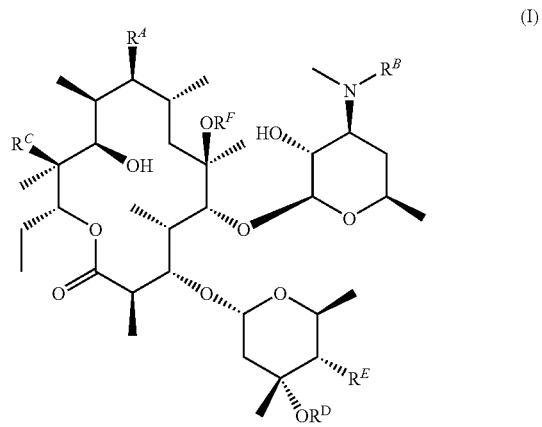

(I)

and the pharmaceutically acceptable salts, solvates, and hydrates thereof, wherein
(A) $R^A$ is
  (i) $OR^1$;
  (ii) $O(CH_2)_m C(\!=\!O)R^2$;
  (iii) $OC(\!=\!O)R^4$;
  (iv) $OS(O_2)N(R^3R^{3A})$;
  (v) $O(CH_2)_n NHR^5$;
  (vi) $N(H)S(O_2)R^6$;
  (vii) $OCH_2CH_2OCH_2CH_2C(\!=\!O)R^2$; or
  (viii) $OCH_2CH_2OCH_2CH_2NHR^5$;
(B) $R^B$ is selected from the group consisting of $C_2$-$C_4$ alkyl, $C_3$-$C_4$ alkenyl, or $C_3$-$C_4$ alkynyl, 3- or 4-membered cycloaliphatic, and 3- or 4-membered heterocycloaliphatic, each member of the group being optionally substituted with one or more substituents selected from the group consisting of OH, CN, and halogen;
(C) $R^C$ is H or OH;
(D) $R^D$ is H or Me;
(E) $R^E$ is H or OH;
and
(F) $R^F$ is H or Me;

wherein
$R^1$ is $C_1$-$C_4$ alkyl, which $C_1$-$C_4$ alkyl is optionally substituted with OH, CN, $O(C_1$-$C_3$ alkyl), halogen, aryl, cycloaliphatic, heteroaryl, or heterocycloaliphatic, said aryl, cycloaliphatic, heteroaryl and heterocycloaliphatic moieties being optionally substituted with $C_1$-$C_4$ alkyl;
$R^2$ is $OR^3$, $N(R^3R^{3A})$, $C_1$-$C_4$ alkyl, $(CH_2)_n OH$, or $C_2$-$C_4$ haloalkyl;
$R^3$ is H, $C_1$-$C_4$ alkyl, or $(CH_2)_n OH$;
$R^{3A}$ is H, $C_1$-$C_4$ alkyl, $(CH_2)_n OH$, $(CH_2)_n O(C_1$-$C_2$ alkyl), $C_2$-$C_4$ haloalkyl, $C_1$-$C_4$ alkyl(aryl), $C_1$-$C_4$ alkyl(heteroaryl), $O(C_1$-$C_4$ alkyl), heteroaryl, or

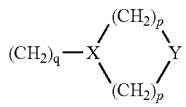

wherein

X is N or CH;

Y is O, S, NH, N(C$_1$-C$_3$ alkyl), CH$_2$, or a bond;

each p is (i) independently 1 or 2 when X is CH$_2$; (ii) 2 when X is N and Y is other than CH$_2$ or a bond; and (iii) independently 1 or 2 when X is N and Y is CH$_2$ or a bond; and q is (i) 0, 1, 2, or 3 when X is CH and (ii) 2 or 3 when X is N;

R$^4$ is N(R$^3$R$^{3A}$) or C$_1$-C$_4$ alkyl;

R$^5$ is S(O$_2$)(C$_1$-C$_4$ alkyl), C(=O)(C$_1$-C$_4$ alkyl), C(=O)aryl, C(=O)(heteroaryl), C(=O)H, or C(=W)NH(C$_1$-C$_4$ alkyl), where W is O or S;

R$^6$ is C$_1$-C$_4$ alkyl, cyclobutyl, cyclopropyl, CF$_3$, or N(R$^3$R$^{3A}$);

m is 1, 2, 3, 4, 5, or 6; and n is, independently for each occurrence thereof, 2, 3 or 4.

In another aspect of this invention, there is provided a method of treating a disease of impaired gastric motility, comprising administering to a subject in need of such treatment a therapeutically effective amount of a compound of the present invention.

In yet another aspect of the invention, there is provided a pharmaceutical composition comprising a compound of this invention and an excipient.

In yet another aspect of the invention, there is provided a method of inducing the contraction of a tissue contractilely responsive to motilin, which method comprises contacting such tissue with a compound according to this invention, in an amount effective to induce such contractions.

In yet another aspect of the invention, there is provided the use of a compound of this invention for the preparation of a medicament for treating a disease of impaired gastric motility.

DETAILED DESCRIPTION OF THE INVENTION

Definitions

"Aliphatic" means a straight- or branched-chain, saturated or unsaturated, non-aromatic hydrocarbon moiety having the specified number of carbon atoms (e.g., as in "C$_3$ aliphatic," "C$_1$-C$_5$ aliphatic," or "C$_1$ to C$_5$ aliphatic," the latter two phrases being synonymous for an aliphatic moiety having from 1 to 5 carbon atoms) or, where the number of carbon atoms is not specified, from 1 to 4 carbon atoms (2 to 4 carbons in the instance of unsaturated aliphatic moieties).

"Alkyl" means a saturated aliphatic moiety, with the same convention for designating the number of carbon atoms being applicable. By way of illustration, C$_1$-C$_4$ alkyl moieties include, but are not limited to, methyl, ethyl, propyl, isopropyl, isobutyl, t-butyl, 1-butyl, 2-butyl, and the like.

"Alkenyl" means an aliphatic moiety having at least one carbon-carbon double bond, with the same convention for designating the number of carbon atoms being applicable. By way of illustration, C$_2$-C$_4$ alkenyl moieties include, but are not limited to, ethenyl (vinyl), 2-propenyl (allyl or prop-2-enyl), cis-1-propenyl, trans-1-propenyl, E- (or Z-)-2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, C$_2$-C$_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings and each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like.

"Alkoxy", "aryloxy", "alkylthio", and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine.

"Aryl" means a hydrocarbon moiety having a mono-, bi-, or tricyclic ring system wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl.

"Heteroaryl" means a moiety having a mono-, bi-, or tricyclic ring system wherein each ring has from 3 to 7 carbon atoms and at least one ring is an aromatic ring containing from 1 to 4 heteroatoms independently selected from from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like.

Where it is indicated that a moiety may be substituted, such as by use of "substituted or unsubstituted" or "optionally substituted" phrasing as in "substituted or unsubstituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein.

"Arylalkyl", (heterocycloaliphatic)alkyl", "arylalkenyl", "arylalkynyl", "biarylalkyl", and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl", "alkenylcycloalkyl", and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl", "haloalkyl", "alkylaryl", "cyanoaryl", and the like mean an alkyl, aryl, etc., moiety, as the case may be, substituted with one or more of the identified substituent (hydroxyl, halo, etc., as the case may be).

By way of illustration, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(cycloalkyl), —O(heterocycloalkyl), —O(aryl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$.

Where a range is stated, as in "$C_1$ to $C_5$ alkyl" or "5 to 10%," such range includes the end points or boundaries of the range.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention.

"Pharmaceutically acceptable salt" means a salt of a compound suitable for pharmaceutical formulation. Where a compound has one or more basic functionalities, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic moieties, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

Compositions and Methods

In a preferred embodiment of the invention, $R^C$ is OH, $R^D$ is Me, $R^E$ is OH, and $R^F$ is H, corresponding to a compound having a structure represented by formula Ia. Such a compound can be made from erythromycin A, a readily available material, as described hereinbelow.

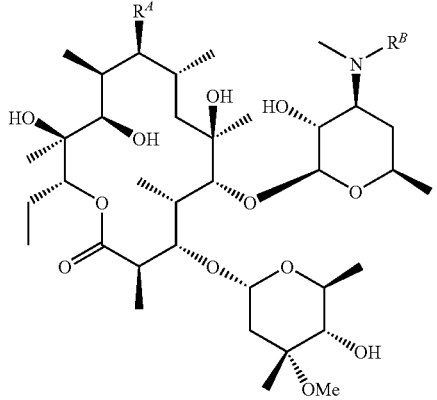

(Ia)

In a preferred embodiment, compounds according to formula Ia have a structure represented by formula Ib:

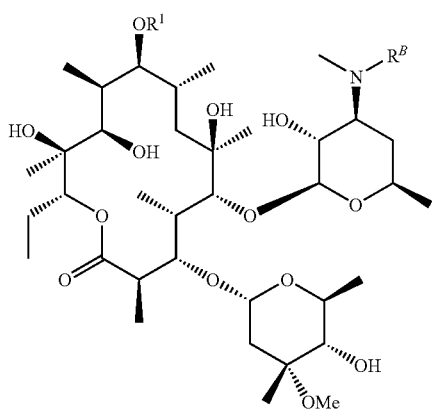

(Ib)

In another preferred embodiment, compounds according to formula Ia have a structure according to formula Ic:

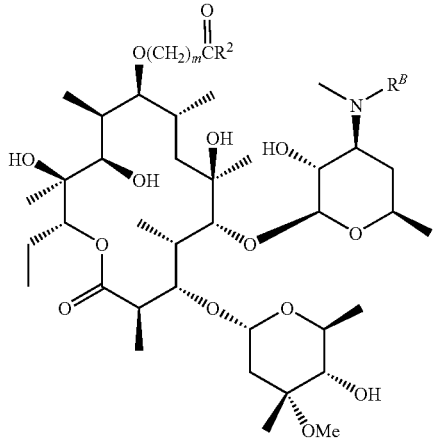

(Ic)

In another preferred embodiment, compounds according to formula Ia have a structure according to formula Ic':

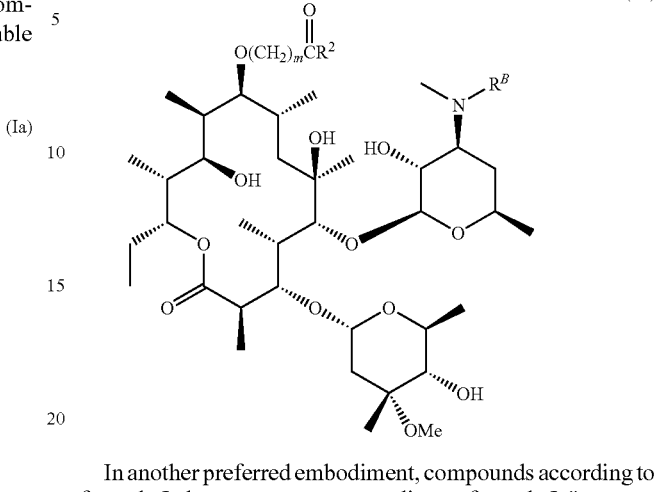

(Ic')

In another preferred embodiment, compounds according to formula Ia have a structure according to formula Ic":

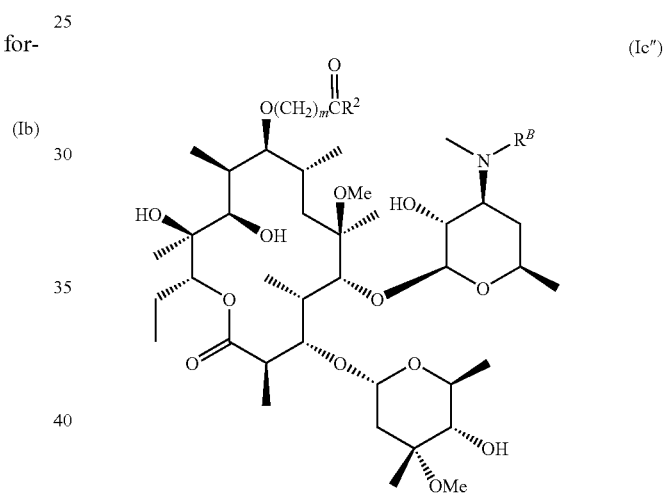

(Ic")

In another preferred embodiment, compounds according to formula Ia have a structure according to formula Ic'":

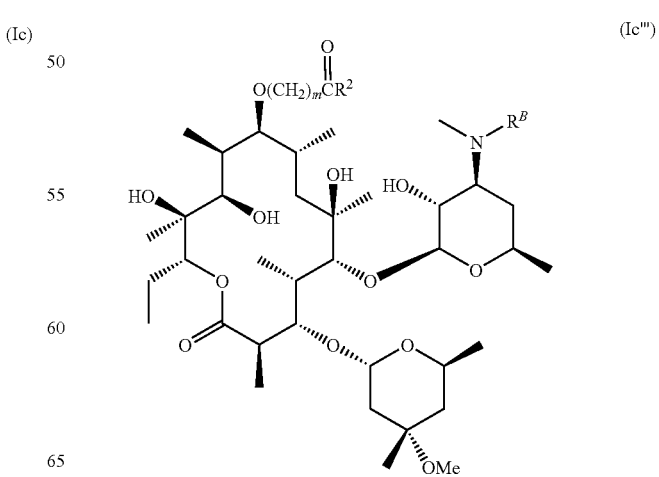

(Ic'")

In another preferred embodiment, compounds according to formula Ia have a structure represented by formula Id:

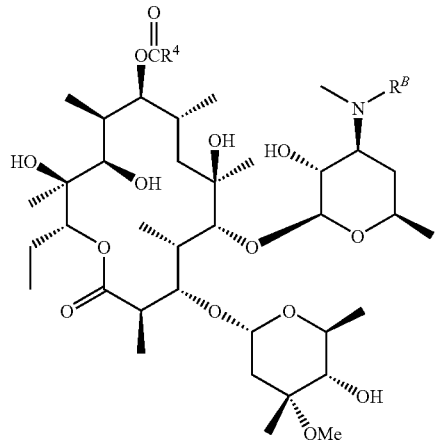
(Id)

In another preferred embodiment, compounds according to formula Ia have a structure represented by formula Id':

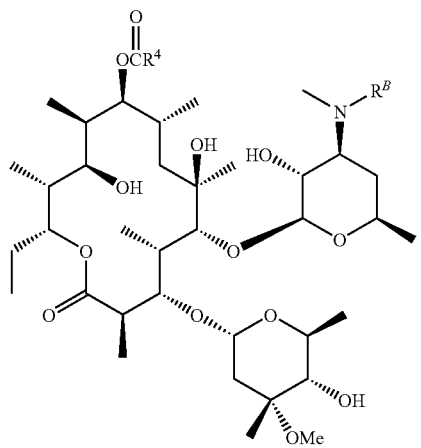
(Id')

In another preferred embodiment, compounds according to formula Ia have a structure represented by formula Ie:

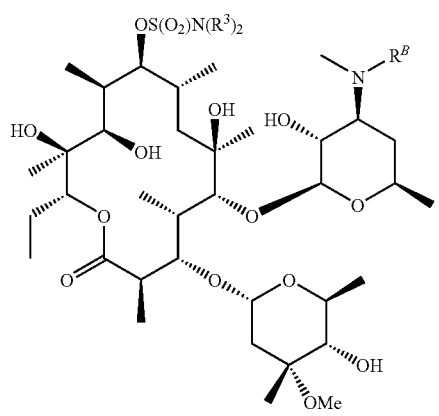
(Ie)

In another preferred embodiment, compounds according to formula Ia have a structure represented by formula If:

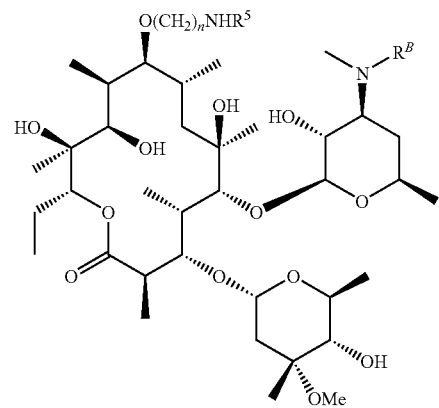
(If)

In another preferred embodiment, compounds according to formula Ia have a structure represented by formula Ig:

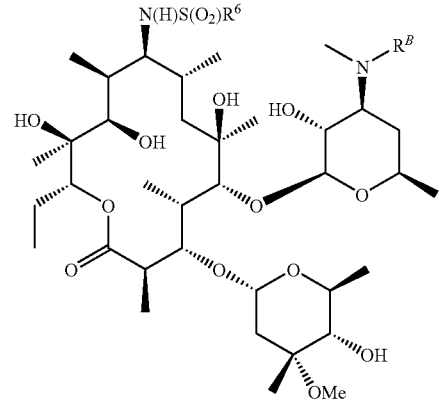
(Ig)

In another preferred embodiment, compounds according to formula Ia have a structure represented by formula Ih:

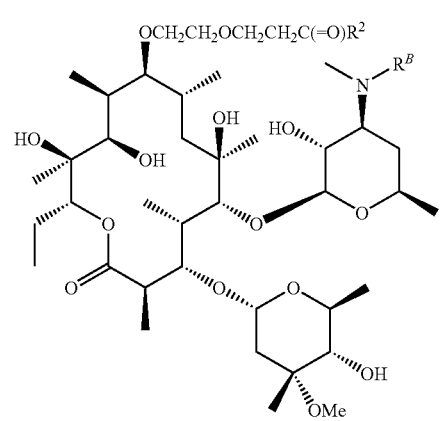
(Ih)

In another preferred embodiment, compounds according to formula Ia have a structure represented by formula Ii:

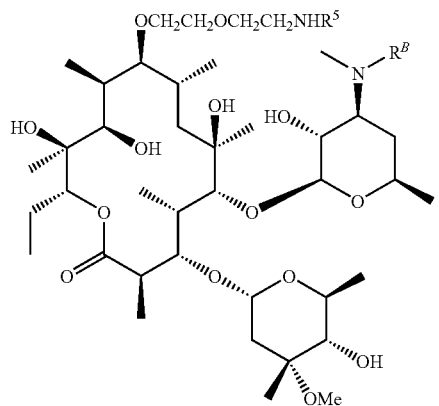
(Ii)

In the foregoing formula Ia through Ii, the various groups $R^A$, $R^B$, $R^1$, $R^2$, etc., where present, have the meanings as defined in respect of formula I in the BRIEF SUMMARY OF THE INVENTION section hereinabove, except when noted otherwise.

Groups $R^A$ having an ether oxygen at the 9-position can be selected from the group consisting of:

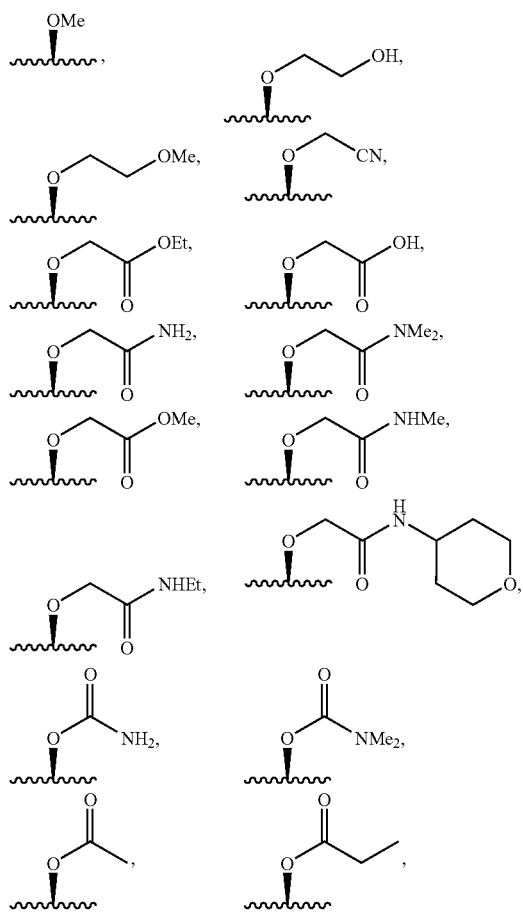

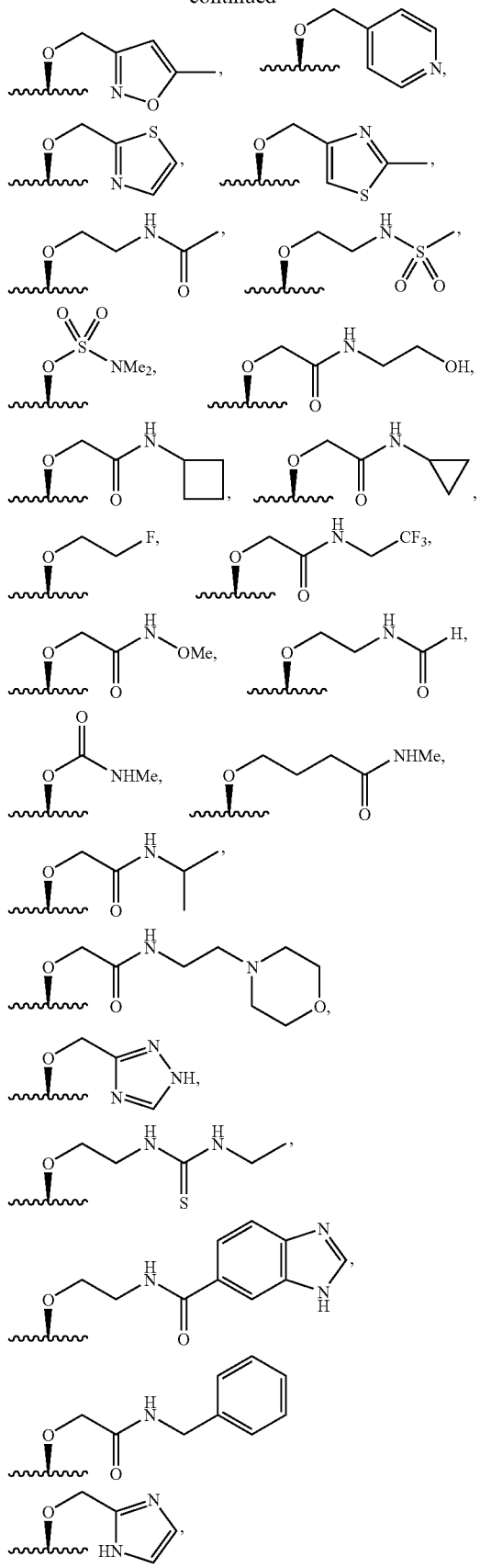

-continued

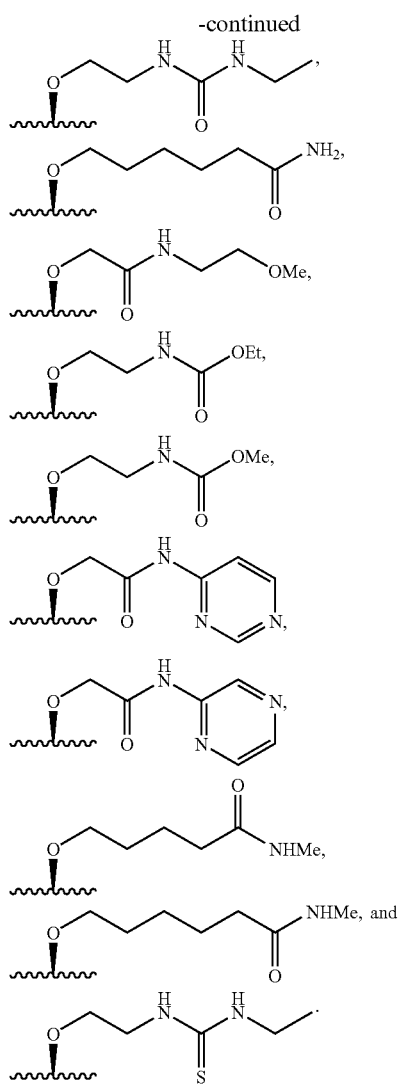

Preferably, such groups $R^A$ are selected from the group consisting of

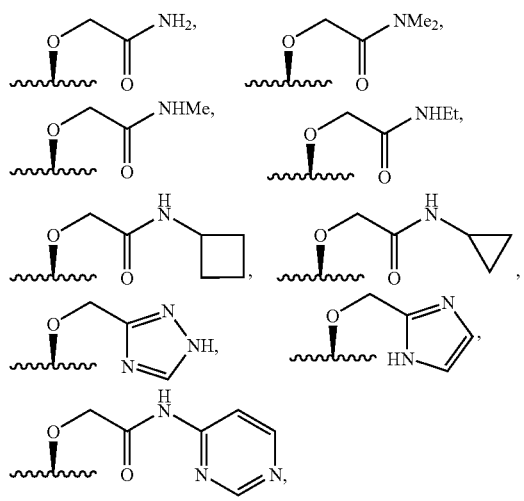

-continued

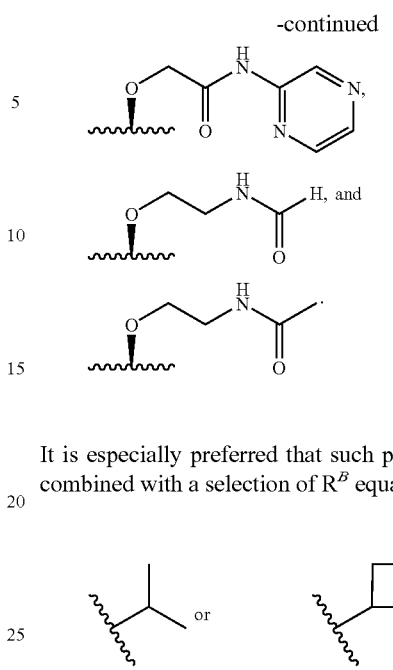

It is especially preferred that such preferred groups $R^A$ are combined with a selection of $R^B$ equals

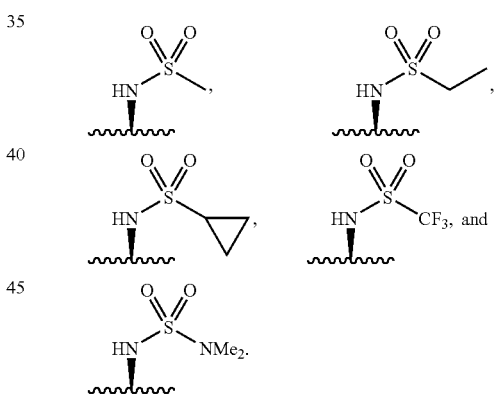

$R^C$ equals H or OH, $R^D$ equals Me, $R^E$ equals H or OH, and $R^F$ equals H or Me.

Preferred groups $R^A$ having a nitrogen at the 9-position are selected from the group consisting of:

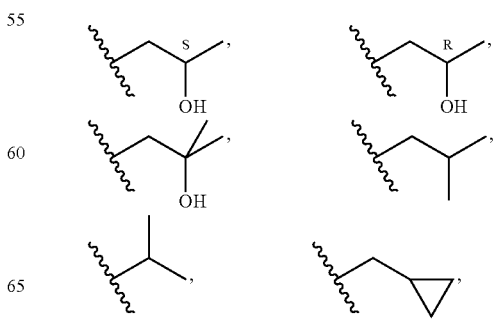

Preferred groups $R^B$ are selected from the group consisting of ethyl, n-propyl, n-butyl, 2-butyl,

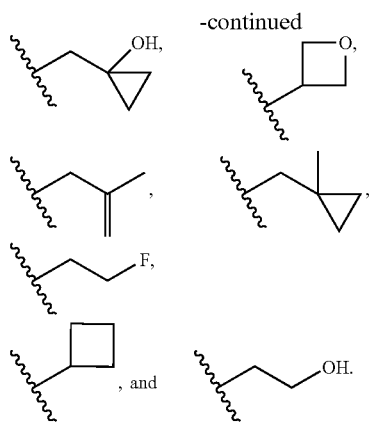

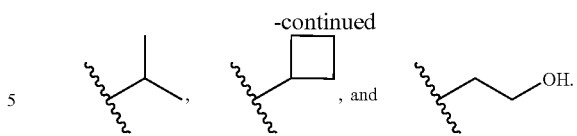

In a preferred embodiments, $R^3$ is H or Me in $OR^3$ and $R^3$ is H in $R^3R^{3.4}$.

Techniques for modification of the desosamine dimethylamino group in erythromycin compounds to replace one of the naturally occurring methyl groups with a different group $R^B$ are taught in, for example, Ashley et al., U.S. Pat. No. 6,750,205 B2 (2004); Ashley et al., US 2002/0094962 A1 (2002); Santi et al., US 2004/0138150 A1 (2004); Carreras et al., US 2005/0113319 A1 (2005); Carreras et al., US 2005/0119195 A1 (2005); and Liu et al., US 2005/0256064 A1 (2005); the disclosures of which are incorporated herein by reference.

Where an alkyl group is substituted, it is preferably substituted at the β-, γ- or δ-carbon, as opposed to the α-carbon.

Specific examples of compounds of this invention according to formula I are tabulated in Table A. (Unless noted otherwise in the "Other" column, $R^C$ is OH, $R^D$ is Me, $R^E$ is OH, and $R^F$ is H.)

More preferably, groups $R^B$ are selected from the group consisting of

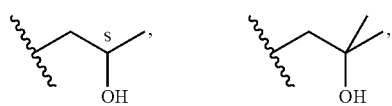

TABLE A

| Compound | $R^A$ | $R^B$ | Other |
|---|---|---|---|
| A-1 | OMe | isopropyl | — |
| A-2 | Same | CH2CH2OH | — |
| A-3 | OCH2CH2OH | isopropyl | — |
| A-4 | Same | cyclobutyl | — |
| A-5 | OCH2CH2OMe | isopropyl | — |
| A-6 | Same | CH2CH(OH)S- | — |
| A-7 | OCH2CN | isopropyl | — |

TABLE A-continued

| Compound | R^A | R^B | Other |
|---|---|---|---|
| A-8 | -O-CH2-C(=O)-OEt | Same | — |
| A-9 | Same | -CH2-CH(SH)(OH)-CH3 (2-hydroxy-propylthio) | — |
| A-10 | Same | -CH2-cyclobutyl | — |
| A-11 | -O-CH2-C(=O)-OH | -CH2-CH(S)(OH)-CH3 | — |
| A-12 | -O-CH2-C(=O)-NH2 | -CH(CH3)2 | — |
| A-13 | Same | -CH2-cyclobutyl | — |
| A-14 | Same | -CH2-CH(S)(OH)-CH3 | — |
| A-15 | -O-CH2-C(=O)-NMe2 | -CH(CH3)2 | — |
| A-16 | Same | -CH2-CH(S)(OH)-CH3 | — |
| A-17 | -O-C(=O)-NH2 | -CH(CH3)2 | — |
| A-18 | -O-C(=O)-NMe2 | Same | — |
| A-19 | -O-S(=O)2-NMe2 | Same | — |
| A-20 | Same | -CH2-CH(S)(OH)-CH3 | — |

TABLE A-continued
| Compound | R^A | R^B | Other |
|---|---|---|---|
| A-21 | 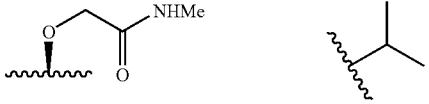 |  | — |
| A-22 | 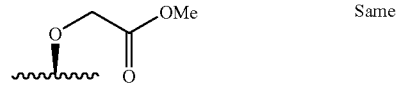 | Same | — |
| A-23 | Same |  | — |
| A-24 |  | Same | — |
| A-25 | 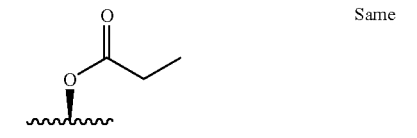 | Same | — |
| A-26 | 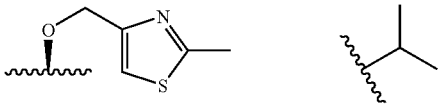 |  | — |
| A-27 | 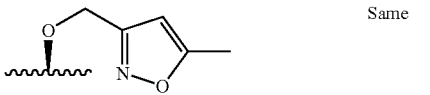 | Same | — |
| A-28 | 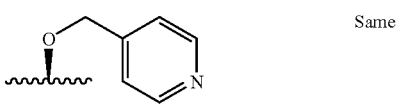 | Same | — |
| A-29 | 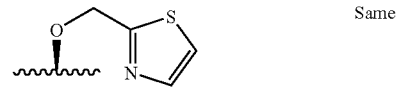 | Same | — |
| A-30 | 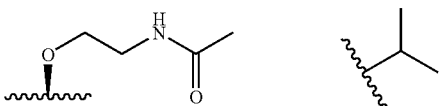 |  | — |
| A-31 |  | Same | — |
| A-32 | 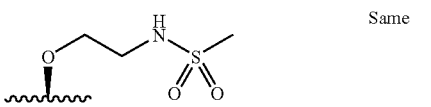 | Same | — |
| A-33 | 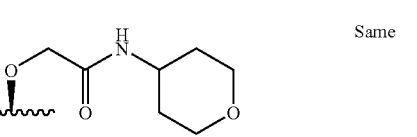 | Same | — |

TABLE A-continued

| Compound | R^A | R^B | Other |
|---|---|---|---|
| A-34 | -O-CH2-C(=O)-NH-CH2CH2-OH | Same | — |
| A-35 | -NH-S(=O)2-CH3 | Same | — |
| A-36 | Same | -CH2CH2-OH | — |
| A-37 | Same | -CH2-C(CH3)2-OH | — |
| A-38 | Same | -CH2-CH(CH3)2 | — |
| A-39 | Same | cyclobutyl-CH2- | — |
| A-40 | -NH-S(=O)2-CH2CH3 | -CH(CH3)2 | — |
| A-41 | -NH-S(=O)2-cyclopropyl | Same | — |
| A-42 | Same | cyclobutyl-CH2- | — |
| A-43 | -NH-S(=O)2-CF3 | -CH(CH3)2 | — |
| A-44 | -NH-S(=O)2-NMe2 | Same | — |
| A-45 | -O-CH2-C(=O)-NH-cyclobutyl | Same | — |

TABLE A-continued

| Compound | R^A | R^B | Other |
|---|---|---|---|
| A-46 | -O-CH2-C(=O)-NH-cyclopropyl | Same | — |
| A-47 | -OMe | cyclobutyl | — |
| A-48 | -O-CH2-C(=O)-NH-CH2CH2-morpholine | isopropyl | — |
| A-49 | -O-CH2CH2-F | Same | — |
| A-50 | -O-(CH2)4-C(=O)-NH2 | Same | — |
| A-51 | -O-CH2-C(=O)-NHMe | cyclobutyl | — |
| A-52 | -O-CH2-C(=O)-NH-CH2-CF3 | isopropyl | — |
| A-53 | -O-CH2-C(=O)-NH-iPr | Same | — |
| A-54 | -O-CH2CH2-NH-C(=O)-NH-Et | Same | — |
| A-55 | -O-CH2-(1H-1,2,4-triazol-3-yl) | Same | — |
| A-56 | -O-CH2-C(=O)-OH | isopropyl | — |
| A-57 | -O-CH2CH2-NH-C(=S)-NH-Pr | Same | — |
| A-58 | -O-CH2CH2-NH-C(=O)-(1H-benzimidazol-5-yl) | Same | — |

TABLE A-continued

| Compound | R^A | R^B | Other |
|---|---|---|---|
| A-59 | -O-CH2-C(=O)-NH-CH2-Ph | Same | — |
| A-60 | -O-CH2-C(=O)-NMe2 | Same | $R^E$ = H |
| A-61 | -O-CH2-C(=O)-NHMe | Same | $R^E$ = H |
| A-62 | -O-CH2-(2-imidazolyl) | Same | — |
| A-63 | -O-CH2-C(=O)-NH-CH2CH2-OMe | Same | — |
| A-64 | -O-CH2CH2-NH-C(=O)-OEt | Same | — |
| A-65 | -O-CH2CH2-NH-C(=O)-OMe | Same | — |
| A-66 | -O-CH2-C(=O)-NHMe | Same | $R^F$ = Me |
| A-67 | -O-CH2CH2-NH-C(=S)-NH-Et | Same | — |
| A-68 | -O-CH2-C(=O)-NHMe | Same | $R^E$ = H |
| A-69 | -O-CH2-C(=O)-N(OMe)H | -CH(CH3)2 | — |
| A-70 | -O-CH2-C(=O)-NH-(2-pyrazinyl) | Same | — |
| A-71 | -O-CH2-C(=O)-NHMe | Same | $R^C$ = H |

TABLE A-continued

| Compound | $R^A$ | $R^B$ | Other |
|---|---|---|---|
| A-72 | —O—CH₂—C(=O)—NMe₂ | Same | $R^C$ = H |
| A-73 | —O—(CH₂)₂—C(=O)—NHMe | Same | — |
| A-74 | —O—(CH₂)₃—C(=O)—NHMe | Same | — |
| A-75 | —O—C(=O)—O—NMe₂ | Same | $R^C$ = H |
| A-76 | —O—(CH₂)₄—C(=O)—NHMe | Same | — |
| A-77 | —O—CH₂—C(=O)—NH-pyrimidin-4-yl | Same | — |
| A-78 | —O—CH₂CH₂—NH—C(=O)H | Same | — |
| A-79 | —O—C(=O)—NHMe | Same | — |

Preferably, compounds of this invention according to formulae I, Ia, Ib, Ic, Ic', Ic", Ic'", Id, Id', Ie, If, Ig, Ih, and Ii have the erythromycin A stereochemistry at the stereochemical centers at positions 2, 3, 4, 5, 6, 8, 10, 11, 12, and 13 in the macrolactone ring; at the stereochemical centers at positions 1', 2', 3', and 5' in the desosamine residue, and at the stereochemical centers at positions 1", 3", 4", and 5" in the cladinose residue.

Particularly preferred compounds of this invention are compounds A-12, A-13, A-15, A-21, A-71, A-74, A-77, and A-78, whose fully written-out structures are:

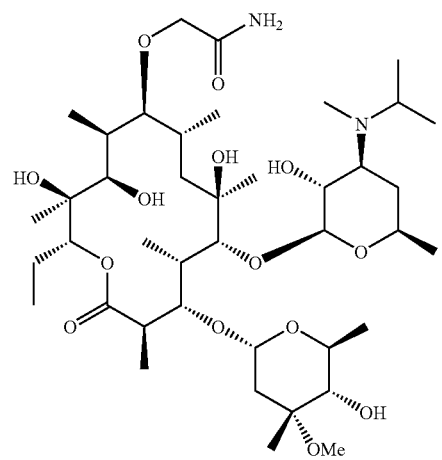

(A-12)

-continued
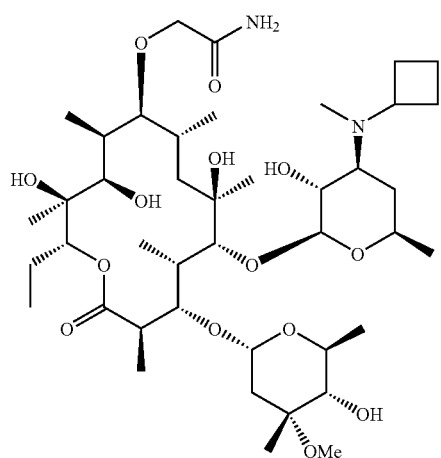
(A-13)
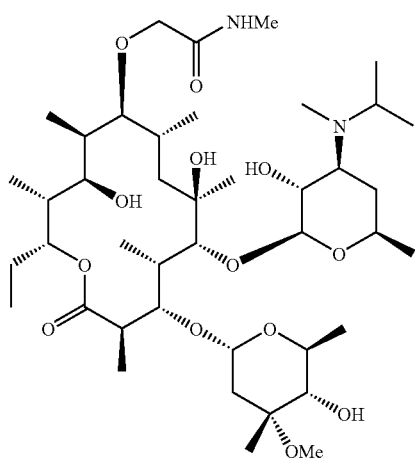
(A-71)
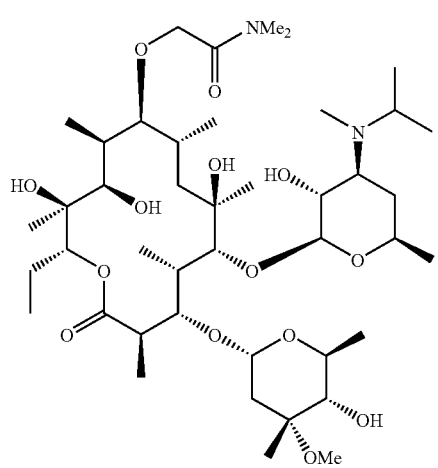
(A-15)
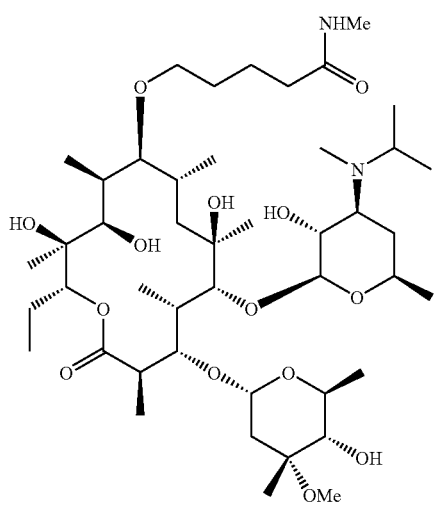
(A-74)
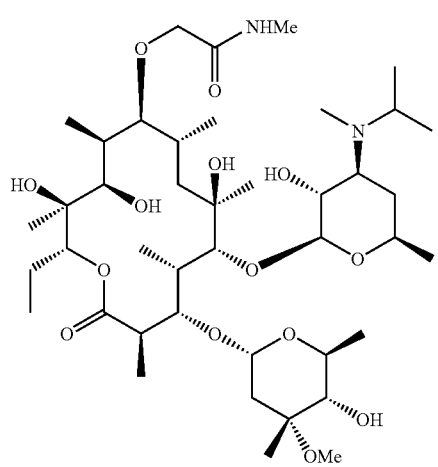
(A-21)
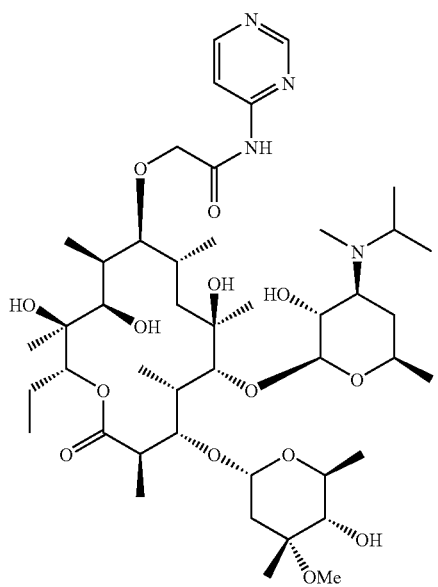
(A-77)

-continued

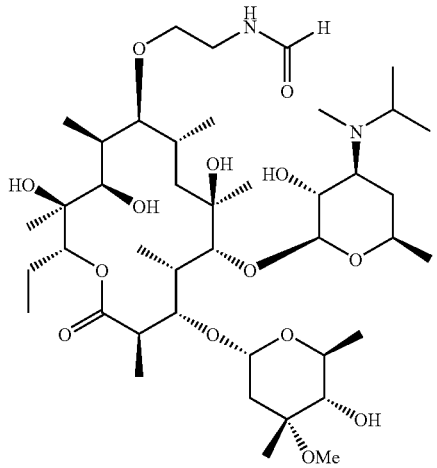

(A-78)

Those skilled in the art will understand that a number of parameters are relevant to the development of motilides. Firstly, the evolution of the erythromycin scaffold in the natural producing organisms has been driven by antibacterial efficacy and not by prokinetic efficacy. Therefore, considerable room remains for optimization of the structure-activity relationship for motilin agonist activity. Secondly, it is in fact undesirable for a motilide to possess antibacterial activity. The GI tract is host to a large population of bacteria, whose exposure to a motilide having antibacterial activity may induce the development in them of resistance to erythromycin antibiotics. Or, a motilide having anti-bacterial activity may kill beneficial gut bacteria. Thus, a motilide desirably has enhanced prokinetic activity engineered in and antibacterial activity engineered out. Thirdly, a drawback commonly found among motilides evaluated to date is their propensity to desensitize the motilide receptor, meaning that, after the initial dose, subsequent doses of a motilide elicit a weaker or no response (tachyphylaxis). Fourthly, stability and bioavailability are concerns—witness the ready degradation of erythromycin A in the stomach and the lack of activity of its secondary degradation product. Fifthly, some compounds in the erythromycin family have been reported to have undesirable pro-arrhythmic effects, including the prolongation of the QT interval and the induction of ventricular arrhythmias. Limiting these effects to an acceptable level is desirable. Thus, there exists a continuing need to develop new motilides, balancing the various different performance requirements.

In addition to the foregoing factors, bioavailability is a factor to be considered. Desirably, a prokinetic agent has rapid bioavailability, enabling it to be taken by a patient shortly before a meal, as opposed to hours before—an advantage in inducing patient compliance. Further, the prokinetic agent should not persist, but, rather, be rapidly cleared out of the system once it has performed its intended function, i.e., have a short half-life.

Another aspect of the present invention provides methods for the use of compounds of this invention in the treatment of impaired gastric motility. In general, methods of using the compounds of the present invention comprise administering to a subject in need thereof a therapeutically effective amount of a compound of the present invention. Illustrative examples of disorders that may be treated with the inventive compounds include but are not limited to gastroparesis, gastroesophageal reflux disease, anorexia, gall bladder stasis, postoperative paralytic ileus, scleroderma, intestinal pseudo-obstruction, gastritis, emesis, and chronic constipation (colonic inertia), in particular gastroparesis and gastroesophageal reflux disease. The subject can be a human or other mammal.

The therapeutically effective amount can be expressed as a total daily dose of the compound or compounds of this invention and may be administered to a subject in a single or in divided doses. The total daily dose can be in amounts, for example, of from about 0.01 to about 10 mg/kg body weight, or more usually, from about 0.1 to about 2 mg/kg body weight. Single dose compositions may contain such amounts or submultiples thereof as to make up the daily dose. In general, treatment regimens according to the present invention comprise administration to a subject in need of such treatment of from about 10 mg to about 1000 mg of the compound(s) of the present invention per day in single or multiple doses.

Typically, the inventive compound will be part of a pharmaceutical composition or preparation that may be in any suitable form such as solid, semisolid, or liquid form. In general, the pharmaceutical preparation will contain one or more of the compounds of the invention as an active ingredient and a pharmaceutically acceptable carrier or excipient. Typically the active ingredient is in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use.

Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

The practice of this invention can be further understood by reference to the following examples, which are provided by way of illustration and not of limitation.

EXAMPLE 1

Synthesis of Intermediate 9

Intermediate 9 (N-desmethyl-N-isopropyl-(9S)-dihydroerythromycin A), used in the synthesis of several compounds of this invention, was synthesized as follows. Intermediate 9 has also been described in Santi et al., US 2004/0138150 A1 (2004), the disclosure of which is incorporated herein by reference.

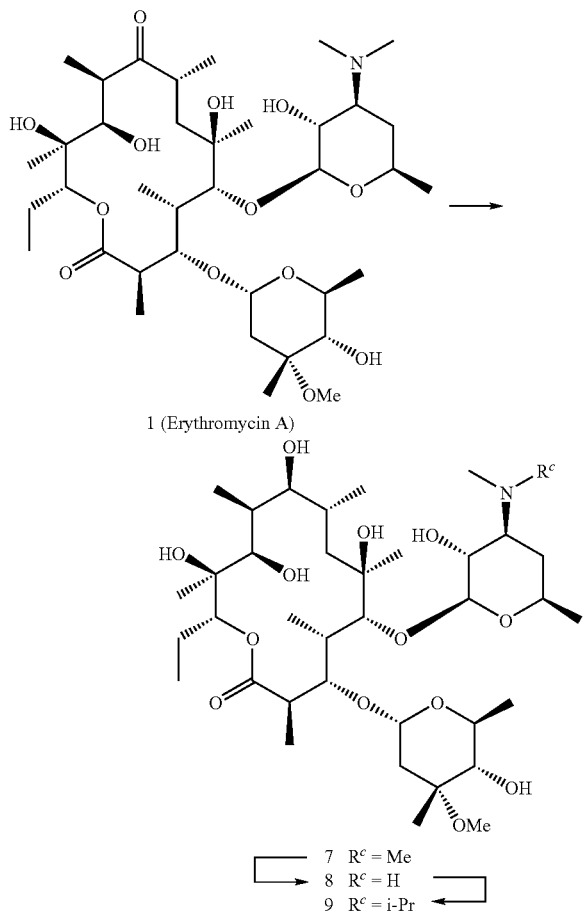

7 R$^c$ = Me
8 R$^c$ = H
9 R$^c$ = i-Pr (9S)-Dihydroerythromycin A (7). Erythromycin A (1) (20.0 g, 27.3 mmol) was dissolved in 2-propanol-ether (1:1 V/V, 400 mL), and cooled to 0° C., sodium borohydride (2.1 g, 54.5 mmol) was added in two aliquots. The mixture was then warmed to room temperature ("RT") and stirred at RT for 3 h. The excess borohydride was destroyed by addition of pH 6.0 phosphate buffer; then triethanolamine (80 mL) was added. After 2 h stirring the mixture was extracted with EtOAc (300 ml×4), dried over MgSO$_4$. The crude was purified by silica gel chromatography using 2:1 hexane-acetone with 1% triethylamine, pure product 7 (17.2 g, 86% yield) was obtained.

Alternatively, the following procedure can be used: A 10-liter three-neck round bottom flask equipped with a mechanical stirrer and internal thermocouple probe was charged with methyl t-butyl ether (2,400 mL) and erythromycin A (400 g, 545 mmol, 1.0 eq.). To this suspension was added MeOH (800 mL). The solution was stirred until became clear (ca. 5-15 min). The solution was cooled with an ice bath to an internal temperature of 2° C. Solid NaBH$_4$ (30.9 g, 816 mmol, 1.5 eq.) was then added in one portion. The resulting suspension was stirred at 0° C. for 1 h, during which time the solution remained clear. After 1 h at 0° C. the ice bath was removed. The mixture was allowed to warm up to 22° C. and stirred for another 3 h. The mixture gradually became opaque. The reaction was complete as monitored by TLC (10% MeOH in CH$_2$Cl$_2$, Silica Gel 60F plates pre-treated with ammonia to neutralize any acidity in the silica gel). Excess NaBH$_4$ was destroyed by careful addition of acetone (120 mL; exothermic reaction: acetone added at a rate to maintain an internal temperature of less than 30° C.) and phosphate buffer (5%, pH 6.0, 120 mL). The reaction turned to a clear solution with some white precipitate. Triethanolamine (400 mL) was added to help decompose the erythromycin-boron complex and the solution was stirred for 1 h. After adding saturated NaHCO$_3$ solution (3,200 mL), the mixture was extracted with EtOAc (3×2,000 mL). The combined extracts were washed once with water and once with brine (2,000 mL each), dried over solid Na$_2$SO$_4$. After removal of solvent, the crude product was dried in a vacuum oven (16 h, 50° C.). A white solid was obtained (416 g, mp 182-185° C.), which was suitable for use in the next step without further purification.

N-Desmethyl-(9S)-dihydroerythromycin A (8). A mixture of (9S)-dihydroerythromycin A 7 (17.2 g, 23.4 mmol) and sodium acetate (9.75 g, 119 mmol) in methanol-water (8:2 V/V, 400 mL) was stirred at 50° C. Iodine (7.25 g, 28.6 mmol) was then added in two aliquots in 30 min interval. During the reaction 3N NaOH (7.9 mL) was added in small portions. Complete reaction was determined by thin-layer chromatographic analysis. After removal of the majority of solvent the mixture was extracted three times with EtOAc and dried over Na$_2$SO$_4$. Crude product 8 (15.6 g) was obtained as a yellow solid, which was used for next step without further purification.

The following alternative procedure can be used: A six-liter three-neck round bottom flask equipped with a mechanical stirrer and internal thermocouple probe was charged with MeOH (2,000 mL), compound 7 from the previous example (150 g, theoretically 197 mmol, 1.0 eq.) and tris(hydroxymethyl)aminomethane (119 g, 5 eq.). The mixture was warmed to 55° C. internal temperature, during which all the materials dissolved. Iodine (75 g, 1.5 eq.) was carefully added, at a rate to prevent the slightly exothermic reaction from raising the internal temperature above 60° C. The mixture was stirred at 55° C. for 5 h. TLC (15% MeOH in CH$_2$Cl$_2$, silica gel plate as described above) indicated completion of the reaction. The reaction mixture was cooled to room temperature. Saturated sodium thiosulfate was used to destroy any excess iodine until the iodine color all disappeared. The mixture was concentrated by removal of about half of the MeOH, taking care to not remove too much of it—this causes precipitation of the product when aqueous solution is subsequently added, the precipitate being difficult to dissolve in the following extractions. The concentrate was diluted with aqueous NaHCO$_3$ (1,500 mL) and extracted with CH$_2$Cl$_2$ (3×1,000 mL). The combined organic layers were washed once with water (1,500 mL) before drying over Na$_2$SO$_4$. The crude product 8 (113 g, mp 118-123° C.) was obtained after removal of solvent and drying in a vacuum oven (16 h, 50° C.). This material was suitable for use in subsequent synthetic procedures without further purification.

Intermediate 9. A mixture of the above crude product 8 (2.50 g, 3.41 mmol), diisopropylethylamine (6.1 mL, 10 equiv), 2-iodopropane (10.2 mL, 30 equiv) in CH$_3$CN (50 mL) was heated in a 70° C. bath for 24 h. H$_2$O and saturated NaHCO$_3$ were added, the solution was extracted three times with EtOAc, dried over MgSO$_4$. The crude product was purified with SiO$_2$ column (3:1 hexane-acetone, 1% TEA) to give pure product 9 (1.80 g, 75% yield for 2 steps). m/z: 765.0 ([M+H]$^+$).

The following alternative procedure for the preparation of intermediate 9 can be used: In a one-liter three neck round bottom flask a solution of product 8 (30 g, 41.5 mmol, 1.0 eq) in MeOH (150 mL) and acetone (30 mL) was stirred with a magnetic stirrer. Acetic acid (3.5 mL, 62.2 mmol, 1.5 eq), followed by NACNBH₃ (5.25 g, 83.3 mmol, 2 eq) were added. The solution was heated with an oil bath and stirred at 50° C. bath temperature for 4 h. A complete reaction was observed as monitored by TLC (1:1 hexane-acetone). After the mixture was cooled to room temperature, phosphate buffer (5%, pH 6.0, 60 mL) was added carefully (rapid H₂ evolution) to quench the excess borohydride. Triethanolamine (100 mL) was then added. The mixture was stirred at RT for 1 hour. The solution was poured into saturated NaHCO₃ solution (500 mL) and the resulting mixture was extracted with EtOAc (2×800 mL). The combined extracts were washed once with brine (600 mL), dried over Na₂SO₄, filtered and concentrated. Crude product (31.8 g) was obtained as white solid after drying under high vacuum for 16 h. Depending on the purity of the precursor product 8, purification prior to subsequent use was or was not needed. If purification was needed, the crude intermediate 9 was dissolved in acetonitrile (100 mL) with heating, followed by addition of water (100 mL) dropwise, with continued heating, until cloudy. The cloudy mixture was allowed to cool to RT, filtered, and vacuum dried at 50° C. for 16 h. This provided pure intermediate 9 (19 g, 24.9 mmol, 47% yield from erythromycin A, mp 127-130° C.) as a white solid.

EXAMPLE 2

Synthesis of Compounds from Intermediate 9

Compound A-1. Sodium hydride (60% dispersion in mineral oil, 12.5 mg) was placed in a dry flask, washed once with pentane (5 mL) and suspended in dimethoxyethane (2 mL). To this suspension a solution of intermediate 9 (200 mg, 0.262 mmol) in dimethoxyethane (2 mL) was added. After stirring at RT for 10 min methyl iodide (2M in t-butyl methyl ether, 0.16 mL) in dimethoxyethane (1 mL) was added. The mixture was stirred at RT overnight. The reaction was quenched by adding saturated aqueous NaHCO₃ solution, extracted three times with CH₂Cl₂, and dried over MgSO₄. The crude product was purified with a silica gel column (4:1 hexanes-acetone, 1% triethylamine) to give compound A-1 (130 mg) as a white solid. m/z: 779.0 ([M+H]⁺); ESI TOF MS m/z 778.5311, calcd for $C_{40}H_{76}NO_{13}$ ([M+H]⁺) 778.5340.

Compound A-3. A mixture of intermediate 9 (80 mg, 0.105 mmol) and KOtBu (17.6 mg, 1.5 eq) in tetrahydrofuran ("THF," 4 mL) was stirred at RT for 30 min. A saturated solution of ethylene oxide in THF (1 mL) was added, and the reaction mixture was stirred for 2 h. LC-MS showed a mixture of starting material and product. Pure compound A-3 (17.5 mg) was obtained after a similar work-up and purification as described above. m/z: 808.6 ([M+H]⁺).

Compound A-5. Compound A-5 was prepared by a method similar to compound A-3, but with 2-bromoethyl methyl ether as the alkylating agent. m/z: 823.0 ([M+H]⁺); ESI TOF MS m/z 822.5533, calcd for $C_{42}H_{80}NO_{14}$ ([M+H]⁺) 822.5573.

Compound A-7. A similar method as that for compound A-3 was used, but with 2-chloroacetonitrile as the alkylating agent. m/z: 804.0 ([M+H]⁺); ESI TOF MS m/z 803.5278, calcd for $C_{41}H_{75}N_2O_{13}$ ([M+H]⁺) 803.5264.

Compound A-8. A similar method as for compound A-3 was used, but with ethyl bromoacetate as the alkylating agent. m/z: 851.0 ([M+H]⁺); ESI TOF MS m/z 850.5499, calcd for $C_{43}H_{80}NO_{15}$ ([M+H]⁺) 850.5523.

Compound A-12. To a solution of intermediate 9 (276 mg, 0.362 mmol) and bromoacetamide (60 mg, 0.435 mmol, 1.2 eq) in 1,2-dimethoxyethane (4 mL) was added KOtBu (1.0 M in THF, 0.54 mL, 1.5 eq). The resulting cloudy mixture was stirred at RT for 3 h, then diluted with EtOAc (50 mL) and NaHCO₃ solution (10 mL). The organic phase was washed with brine (10 mL) and the aqueous phase was extracted with EtOAc (2×10 mL). The combined organic layers were dried over Na₂SO₄, filtered and concentrated. The residue was purified by silica gel column chromatography (10% to 95% of acetone in hexanes, with 1% triethylamine) to yield compound A-12 (220 mg, 73%) as a white solid. m/z: 822.0 ([M+H]⁺); ESI TOF MS m/z 821.5385, calcd for $C_{41}H_{77}N_2O_{14}$ ([M+H]⁺) 821.5369.

Compound A-15. A similar method as that for compound A-12 was used, except that the bromoacetamide was replaced by 2-chloro-N,N-dimethylacetamide. m/z: 850.0 ([M+H]⁺); ESI TOF MS m/z 849.5673, calcd for $C_{43}H_{81}N_2O_{14}$ ([M+H]⁺) 849.5682.

Compound A-17. A modified version of the method for preparing compound A-12 was used. To a solution of intermediate 9 (256 mg, 0.335 mmol) in 1,2-dimethoxyethane (2 mL) was added KOtBu (1.0 M in THF, 1.06 mL, 3.0 eq). The resulting mixture was stirred at room temperature for 10 min before it was cooled to −78° C. Trichloroacetyl isocyanate (0.096 mL, 2.4 eq) was added. The reaction mixture was slowly warmed up to RT in 3 h. The trichloroacetyl group was hydrolyzed during the same aqueous work-up as reported for compound A-12, to yield compound A-17. m/z: 808.0 ([M+H]⁺); ESI TOF MS m/z 807.5212, calcd for $C_{40}H_{75}N_2O_{14}$ ([M+H]⁺) 807.5213.

Compound A-18. A similar method as that for compound A-12 was used, but with dimethylcarbamoyl chloride replacing bromoacetamide. m/z: 836.0 ([M+H]⁺); ESI TOF MS m/z 835.5533, calcd for $C_{42}H_{79}N_2O_{14}$ ([M+H]⁺) 835.5526.

Compound A-19. A similar method as that for compound A-12 was used, but with dimethylsulfamoyl chloride instead of bromoacetamide. m/z: 872.0 ([M+H]⁺); ESI TOF MS m/z 871.5218, calcd for $C_{41}H_{78}N_2O_{15}S$ ([M+H]⁺) 871.5196.

Compound A-21. A similar method as for compound A-12 was used, but with 2-bromo-N-methylacetamide instead of bromoacetamide. m/z: 836 ([M+H]⁺), 678; ESI TOF MS m/z 835.5498, calcd for $C_{42}H_{78}N_2O_{14}$ ([M+H]⁺) 835.5526. ¹³C NMR (CDCl₃) δ 177.3, 170.3, 101.8, 94.4, 94.2, 83.7, 77.6, 77.4, 77.1, 75.5, 74.2, 72.7, 72.6, 69.9, 69.7, 69.3, 65.6, 61.8, 52.5, 49.2, 44.0, 43.6, 38.1, 34.3, 32.7, 32.6, 32.2, 30.9, 25.5, 22.1, 22.0, 21.5, 21.1, 21.0, 20.2, 19.1, 17.4, 16.6, 14.3, 12.9, 11.2, 9.0 ppm.

The following alternative procedure can be used: In a five-liter three neck round bottom flask equipped with mechanical stirrer and internal thermocouple temperature probe a solution of intermediate 9 (156.7 g, 205 mmol), N-methyl bromoacetamide (37.4 g, 246 mmol, 1.2 eq) in dry THF (1800 mL) was cooled with an ice bath. With stirring at 0° C. internal temperature under nitrogen, solid potassium tert-butoxide (25.3 g, 226 mmol, 1.1 eq) was added as one batch. The mixture was stirred at 0° C. for 1 h. Completion of the reaction was monitored by TLC (1:2 hexane-acetone, silica gel 60 F, ammonia pre-treated). The reaction mixture was quenched by adding saturated NaHCO₃ solution (300 mL). The mixture was partitioned between dilute NaHCO₃ solution (2,500 mL) and EtOAc (1,500 mL). The aqueous layer was extracted with ethyl acetate (2×1500 mL). The combined organic layers were dried over Na₂SO₄. Crude product (178.1 g) was obtained as slightly yellow solid, which was then purified with silica gel column (2,800 g Silica Gel 60 F, 20-40% acetone in hexane, 1% triethylamine) to give compound A-21 (135 g, 79% yield). To remove traces of solvents and triethylamine, the product was repeatedly dissolved in dichloromethane and dried in a rotary evaporator (4 cycles) and dried in a vacuum oven (16 h, 50° C.) to give the final product (mp 106-108° C.).

Optionally, the known reactant N-methyl bromoacetamide can be prepared as follows: A 10 liter three neck round bottom flask equipped with mechanical stirrer and internal thermocouple temperature probe was charged with THF (3,200 mL), methylamine (2 M solution in THF, 692 mL, 1.38 mol, 1.5 eq), NaHCO$_3$ (155 g, 1.845 mol, 2 eq) and triethylamine (128.2 mL, 922 mmol, 1.0 eq). The suspension was cooled with a dry ice-acetone bath to an internal temperature –70° C. 2-Bromoacetyl bromide (79.8 mL, 922 mmol, 1.0 eq) was added dropwise, with stirring. After the addition the dry ice bath was removed. The mixture was warmed up to room temperature. The resulting yellow suspension was quenched with saturated NaHCO$_3$ (3200 mL), and extracted with ethyl acetate (2×3,200 mL). The combined organics were washed with saturated ammonium chloride (2,000 mL), and brine (2,000 mL), dried over Na$_2$SO$_4$. After concentration under vacuum the red colored crude product (82 g) was dissolved in CH$_2$Cl$_2$ (100 mL) and passed through a pad of silica (1,600 g), eluting with 50% ethyl acetate/hexane. Fractions containing product (TLC with 30% ethyl acetate/hexane, visualized with iodine) were combined and concentrated under vacuum (note 1) to afford pure product as a low melting point solid (77.5 g, 55% yield).

Compound A-22. A similar method as that for compound A-12 was used, but with methyl bromoacetate as the alkylating agent. m/z: 836.5 ([M+H]$^+$); ESI TOF MS m/z 836.5343, calcd for C$_{33}$H$_{50}$NO$_8$ ([M+H]$^+$) 836.5366.

Compound A-26. A similar method as for compound A-12 was used, but with 4-(iodomethyl)-2-methylthiazole as the alkylating agent. m/z: 876.0 ([M+H]$^+$), ESI TOF MS m/z 875.5310, calcd for C$_{44}$H$_{79}$N$_2$O$_{13}$S ([M+H]$^+$) 875.5297.

Compound A-27. Similar method as for compound A-12 was used, but with 3-(bromomethyl)-5-methylisoxazole as the alkylating agent. m/z: 860.0 ([M+H]$^+$), ESI TOF MS m/z 859.5494, calcd for C$_{44}$H$_{79}$N$_2$O$_{14}$ ([M+H]$^+$) 859.5526.

Compound A-28. Similar method as for compound A-12 was used, but with 4-(bromomethyl)pyridine as the alkylating agent. m/z: 856.0 ([M+H]$^+$), ESI TOF MS m/z 855.5613, calcd for C$_{45}$H$_{79}$N$_2$O$_{13}$ ([M+H]$^+$) 855.5577.

Compound A-29. Similar method as for compound A-12 was used, but with 2-(iodomethyl)thiazole as the alkylating agent. m/z: 862.0 ([M+H]$^+$), ESI TOF MS m/z 861.5181, calcd for C$_{43}$H$_{77}$N$_2$O$_{13}$S ([M+H]$^+$) 861.5141.

Compound A-31. A similar method as that for compound A-12 was used, with 2-bromo-N-ethylacetamide as the alkylating agent instead. m/z: 850 ([M+H]$^+$).

Compound A-33. A similar method as that for compound A-12 was used, but with 2-bromo-N-(4-tetrahydropyranyl) acetamide as the alkylating agent. m/z: 906 ([M+H]$^+$); ESI TOF MS m/z 905.5957, calcd for C$_{46}$H$_{84}$N$_2$O$_{15}$ ([M+H]$^+$) 905.5946.

Compound A-34. A similar method as that for compound A-12 was used, with 2-bromo-N-[2-(tert-butyldimethylsilyloxy)ethyl]acetamide as the alkylating agent. The 9-alkylated product (0.101 g, 0.104 mmol) was dissolved in THF (1.0 mL) and cooled to 0° C. Tetrabutylammonium fluoride (0.020 g, 0.114 mmol, 1.1 eq) was added and the solution stirred at 0° C. for 2.5 h before adding NaHCO$_3$ (15 mL). The organic phase was extracted with EtOAc (3×15 mL), combined, washed with brine (25 mL), dried (Na$_2$SO$_4$) and concentrated under reduced pressure. Column chromatography (silica, 55% acetone-hexane, 1% triethylamine) yielded compound A-34 (0.063 g) as a white solid; m/z: 866 ([M+H]$^+$); ESI TOF MS m/z 865.5655, calcd for C$_{43}$H$_{80}$N$_2$O$_{15}$ ([M+H]$^+$) 865.5632.

Compound A-45. A similar method as that for compound A-12 was used, but with 2-bromo-N-cyclobutylacetamide as the alkylating agent. m/z: 876 ([M+H]$^+$), 718; ESI TOF MS m/z 874.5833, calcd for C$_{45}$H$_{83}$N$_2$O$_{14}$ ([M+H]$^+$) 874.5839.

Compound A-46. A similar method as that for compound A-12 was used, but with 2-bromo-N-cyclopropylacetamide as the alkylating agent. m/z: 862 ([M+H]$^+$), 703; ESI TOF MS m/z 861.5695, calcd for C$_{44}$H$_{81}$N$_2$O$_{14}$ ([M+H]$^+$) 861.5682.

Compound A-48. A similar method as that for compound A-12 was used, with 2-bromo-N-(2-morpholino)ethylacetamide as the alkylating agent. m/z: 934.6 ([M+H]$^+$).

Compound A-49. A similar method as that for compound A-12 was used, with 1-iodo-2-fluoroethane as the alkylating agent. m/z: 811.0 ([M+H]$^+$); ESI TOF MS m/z 810.5374, calcd for C$_{39}$H$_{74}$NO$_{14}$ ([M+H]$^+$) 810.5385.

Compound A-50. A similar method as that for compound A-12 was used, with 6-bromohexaneamide as the alkylating agent. m/z: 877.6 ([M+H]$^+$); ESI TOF MS m/z 877.5995, calcd for C$_{44}$H$_{80}$NO$_{15}$ ([M+H]$^+$) 877.5999.

Compound A-52. A similar method as that for compound A-12 was used, with 2-bromo-N-(trifluoroethyl)acetamide as the alkylating agent. m/z: 904 ([M+H]$^+$), ESI TOF MS m/z 903.5385, calcd for C$_{43}$H$_{77}$N$_2$O$_{14}$F$_3$ ([M+H]$^+$) 903.5400.

Compound A-53. A similar method as that for compound A-12 was used, with 2-bromo-N-isopropylacetamide as the alkylating agent. m/z: 864 ([M+H]$^+$), ESI TOF MS m/z 863.5818, calcd for C$_{44}$H$_{82}$N$_2$O$_{14}$ ([M+H]$^+$) 863.5839.

Compound A-55. A similar method as that for compound A-12 was used, with 3-chloromethyl-2-trityl-1,2,4-triazole as the alkylating agent. A methanol (6 mL) solution containing the initial alkylated product (170 mg), pyridine hydrochloride (7 mg), and pyridinium para-toluenesulfonate (10 mg) was kept at 50° C. overnight with stirring. The reaction was quenched with saturated aqueous NaHCO$_3$ solution (20 mL), and was extracted with chloroform/methanol (5/1) (20 mL, 3×). The combined organic extracts were dried over sodium sulfate. Flash chromatography on silica gel (100:10:0.5 CH$_2$CCl$_2$:MeOH:NH$_4$OH) afforded compound A-55 as a white solid (35 mg), m/z: 846.0 ([M+H]$^+$).

Compound A-59. A similar method as that for compound A-12 was used, with N-benzyl bromoacetamide as alkylating agent instead of bromoacetamide. m/z: 912 ([M+H]$^+$), 754; ESI TOF MS m/z 911.5813, calcd for C$_{48}$H$_{82}$N$_2$O$_{14}$ ([M+H]$^+$) 911.5839.

Compound A-62. A similar method as that for compound A-12 was used, with 2-chloromethylimidazole hydrochloride as alkylating agent instead of bromoacetamide. m/z: 845.0 ([M+H]$^+$).

Compound A-63. A similar method as that for compound A-12 was used, with N-(2-methoxy)ethyl bromoacetamide as as alkylating agent instead of bromoacetamide. m/z: 879.6 ([M+H]$^+$).

Compound A-69. A similar procedure to that reported for compound A-12 was used, reaction on a 0.085 mmol scale with bromoacetic acid 2-(trimethylsilyl)ethyl ether yielded the 9-O-acetic acid-2-(trimethylsilyl)ether ester (0.045 g, 57%), which was dissolved in N,N-dimethylformamide (DMF, 1.0 mL) and cooled to 0° C. before adding tetrabutylammonium fluoride (0.015 g, 0.059 mmol, 1.2 eq). The solution was stirred at 0° C. for 5 hours before adding ethyl-(3-dimethylamino)propylcarbodiimide (0.014 g, 0.074 mmol, 1.5 eq), hydroxybenzotriazole (0.013 g, 0.098 mmol, 2.0 eq) and methoxylamine hydrochloride (0.008 g, 0.098 mmol, 2.0 eq). The solution was stirred at room temperature for 18 hours before diluting with EtOAc (15 mL) and washing with NaHCO$_3$ (15 mL) and brine (15 mL). The organic phases were dried (Na$_2$SO$_4$) and concentrated under reduced pressure. Column chromatography (silica, 30→50% acetone-hexane, 1% triethylamine) yielded compound A-69 (0.009 g, 22%) as a white solid. m/z: 852 ([M+H]+), 754; ESI TOF MS m/z 851.5490, calcd for $C_{42}H_{78}N_2O_{15}$ ([M+H]+) 851.5475.

Compound A-70. A similar method as that for compound A-12 was used, with N-pyrazyl bromoacetamide as alkylating agent instead of bromoacetamide. m/z: 900 ([M+H]+), 742; ESI TOF MS m/z 899.5563, calcd for $C_{45}H_{78}N_4O_{14}$ ([M+H]+) 899.5587.

Compound A-73. A similar method as that for compound A-12 was used, with N-methyl 3-bromopropionamide as alkylating agent instead of bromoacetamide. m/z: 864 ([M+H]+), 706; ESI TOF MS m/z 863.5814, calcd for $C_{44}H_{82}N_2O_{14}$ ([M+H]+) 863.5839.

Compound A-74. A similar method as that for compound A-12 was used, with N-methyl 5-bromovalerylamide as alkylating agent instead of bromoacetamide. m/z: 878 ([M+H]+), 720; ESI TOF MS m/z 877.5978, calcd for $C_{45}H_{84}N_2O_{14}$ ([M+H]+) 877.5995.

Compound A-76. A similar method as that for compound A-12 was used, with N-methyl 6-bromohexanoylamide as alkylating agent instead of bromoacetamide. m/z: 892 ([M+H]+), 734; ESI TOF MS m/z 891.6127, calcd for $C_{46}H_{86}N_2O_{14}$ ([M+H]+) 891.6152.

Compound A-77. A similar method as that for compound A-12 was used, with N-pyramidinyl bromoacetamide as alkylating agent instead of bromoacetamide. m/z: 922 ([M+Na]+), 900 ([M+H]+), 742; ESI TOF MS m/z 899.5552, calcd for $C_{45}H_{78}N_4O_{14}$ ([M+H]+) 899.5587.

Compound A-79. Potassium tert-butoxide (0.17 mL of a 1M solution in THF, 0.167 mmol, 1.5 eq) was added to a solution of intermediate 9 (0.085 g, 0.111 mmol, 1.0 eq) in dimethoxyethane (1.0 mL). The solution was stirred at RT for 10 min, before adding carbonyldiimidazole (0.022 g, 0.134 mmol, 1.2 eq). The solution was stirred at room temperature for 1 hour before adding methylamine (0.024 mL of a 33% solution in EtOH, 0.134 mmol, 1.2 eq). The resulting solution was stirred at RT for 1.5 hours before pouring into NaHCO3 (25 mL) and extracting with EtOAc (4×20 mL). The combined organics were dried (Na2SO4) and concentrated under reduced pressure. Column chromatography (silica, 30% acetone-hexane, 0.5% Et3N) yielded the compound A-79 (0.010 g, 11%) as a white solid. m/z: 822 ([M+H]+), 664; ESI TOF MS m/z 821.5339, calcd for $C_{41}H_{76}N_2O_{14}$ ([M+H]+) 821.5369.

EXAMPLE 3

Compound A-2

Compound A-2. 9S-Dihydroerythromycin A 7 was methylated as described above in connection with compound A-1, using 2-iodoethanol. The desosamine moiety of the resulting 9-methoxy product was desmethylated and alkylated to give compound A-2. m/z: 780.5 ([M+H]+); ESI TOF MS m/z 780.5104, calcd for $C_{39}H_{74}NO_{14}$ ([M+H]+) 780.5113.

EXAMPLE 4

Intermediate 10

Intermediate 10 (N-desmethyl-N-cyclobutyl-(9S)-dihydroerythromycin A) was used in the synthesis of compounds of this invention.

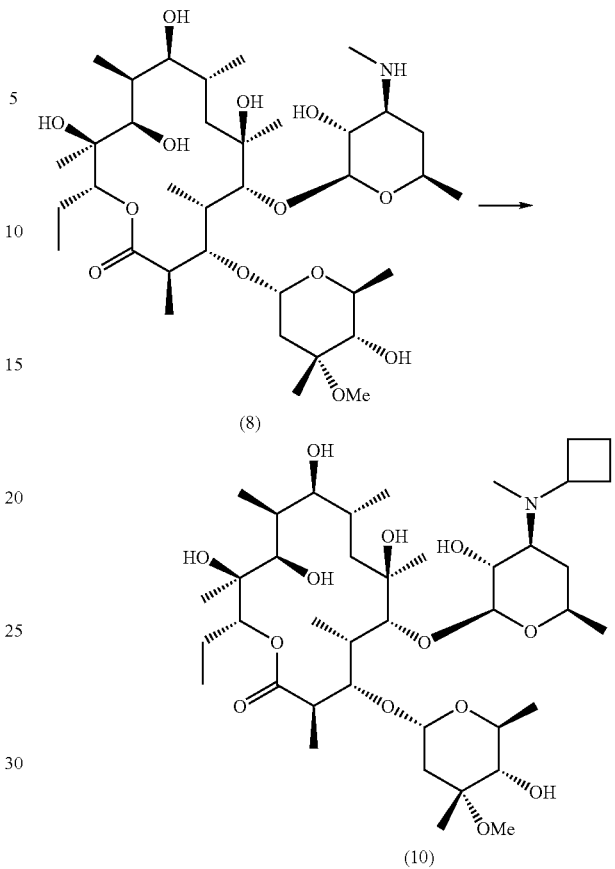

A mixture of N-desmethyl-(9S)-dihydroerythromycin A 8 (4.96 g, 6.87 mmol), cyclobutanone (1.03 mL, 2 eq), sodium cyanoborohydride (863 mg, 2 eq) and HOAc (1.57 mL, 4 eq) in methanol (40 mL) was stirred at 50° C. for 4 h. Water was added, followed by triethanolamine (20 mL). After 2 h of stirring the mixture was extracted three times with EtOAc, dried over MgSO4. The crude product was purified using a SiO2 column (3:1 to 2:1 hexane-acetone, 1% TEA) to give pure intermediate 10 (3.70 g). m/z: 777.0 ([M+H]+).

EXAMPLE 5

Synthesis of Compounds from Intermediate 10

Compound A-4. A similar method as that for the preparation of compound A-3 was used, with intermediate 10 as starting material. m/z: 820.6 ([M+H]+).

Compound A-10. A similar method as that for compound A-3 was used, with intermediate 10 as starting material and ethyl bromoacetate as the alkylating agent. m/z: 863.0 ([M+H]+); ESI TOF MS m/z 862.5523, calcd for $C_{44}H_{80}NO_{15}$ ([M+H]+) 862.5515.

Compound A-13. A similar method as that for compound A-12 was used, with intermediate 10 as the starting material. m/z: 834.0 ([M+H]+); ESI TOF MS m/z 833.5348, calcd for $C_{42}H_{77}N_2O_{14}$ ([M+H]+) 833.5369.

Compound A-23. A similar method as that for compound A-22 was used, with intermediate 10 as starting material. m/z: 849.0 ([M+H]+); ESI TOF MS m/z 848.5366, calcd for $C_{43}H_{78}NO_{15}$ ([M+H]+) 848.5367.

Compound A-24. To a solution of intermediate 10 (100 mg, 0.127 mmol) in ethyl acetate (10 mL), was added acetic anhydride (61 µL, 0.65 mmol, 5 eq) and K2CO3. The mixture was stirred at RT overnight. The reaction was diluted with EtOAc (100 mL), was then washed with saturated aq. NaHCO$_3$ (3×50 mL), dried over Na$_2$SO$_4$, filtered, and evaporated to dryness. The product (95 mg) was obtained after silica gel column chromatography (5% to 35% acetone in hexanes, 1% triethylamine). This product was then dissolved in methanol (3 mL) and heated at 50° C. overnight. The solvent was removed and compound A-24 (80 mg) was obtained after silica gel column chromatography (5% to 35% acetone in hexanes, 1% triethylamine). m/z: 819.0 ([M+H]$^+$).

Compound A-25. A similar protocol as that for compound A-24 was used, except that the acetic anhydride was replaced by propionic anhydride. m/z: 833.0 ([M+H]$^+$).

Compound A-47. A similar method as that for compound A-1 was used, but with intermediate 10 instead of intermediate 9. m/z: 791.0 ([M+H]$^+$); ESI TOF MS m/z 790.5311, calcd for C$_{41}$H$_{76}$NO$_{13}$ ([M+H]$^+$) 790.5301.

Compound A-51. A similar method as that for compound A-12 was used, with intermediate 10 the as starting material and 2-bromo-N-methylacetamide as the alkylating agent. m/z: 848.0 ([M+H]$^+$); ESI TOF MS m/z 847.5529, calcd. for C$_{43}$H$_{79}$N$_2$O$_{14}$ ([M+H]$^+$) 847.5526.

EXAMPLE 6

Intermediate 11

Intermediate 11 (N-desmethyl-N-(2-hydroxypropyl)-(9S)-dihydroerythromycin A) was used in the synthesis of compounds of this invention.

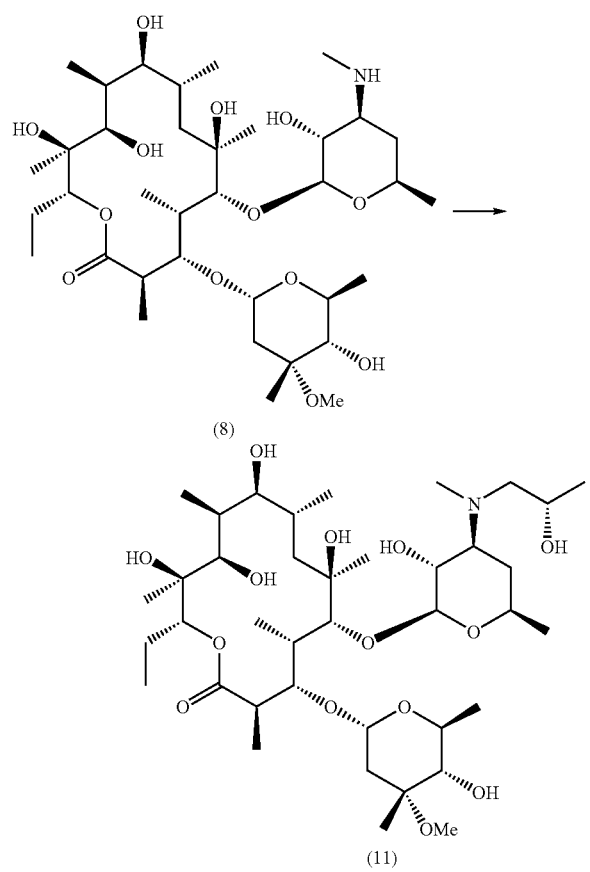

A solution of N-desmethyl-(9S)-dihydroerythromycin A 8 (see Example 1, 357 mg, 0.494 mmol) and (S)-propylene oxide (0.35 mL, 10 eq) in methanol (10 mL) was stirred at RT for 24 h. Completion of the reaction was determined by TLC. After evaporation of the solvent, the crude product was purified with silica gel column (5% to 45% acetone in hexane, 1% triethylamine) to give pure intermediate 11 (271 mg, 70%). m/z: 781.0 ([M+H]$^+$); ESI TOF MS m/z 780.5099, calcd for C$_{39}$H$_{74}$NO$_{14}$ ([M+H]$^+$) 780.5104.

EXAMPLE 7

Synthesis of Compounds from Intermediate 11

Compound A-6. A similar method as for compound A-3 was used, with intermediate 11 as the starting material and 2-bromoethyl methyl ether as the alkylating agent. m/z: 839.0 ([M+H]$^+$); ESI TOF MS m/z 838.5489, calcd for C$_{42}$H$_{80}$NO$_{15}$ ([M+H]$^+$) 838.5522.

Compound A-9. A similar method as that for compound A-3 was used, with intermediate 9 as starting material and ethyl bromoacetate as the alkylating agent. m/z: 867.0 ([M+H]$^+$); ESI TOF MS m/z 866.5433, calcd for C$_{43}$H$_{80}$NO$_{16}$ ([M+H]$^+$) 866.5472.

Compound A-14. A similar method as that for compound A-12 was used, with intermediate 11 the as starting material. m/z: 838.0 ([M+H]$^+$); ESI TOF MS m/z 875.4834, calcd for C$_{41}$H$_{76}$N$_2$O$_{15}$K ([M+K]$^+$) 875.4877.

Compound A-16. A similar method as that for compound A-12 was used, with intermediate 11 as starting material and 2-chloro-N,N-dimethylacetamide as the alkylating agent. m/z: 866.0 ([M+H]$^+$); ESI TOF MS m/z 865.5630, calcd for C$_{43}$H$_{81}$N$_2$O$_{15}$ ([M+H]$^+$) 865.5632.

Compound A-20. A similar method as that for compound A-12 was used, with intermediate 11 as starting material and dimethylsulfamoyl chloride instead of bromoacetamide. m/z: 888.0 ([M+H]$^+$); ESI TOF MS m/z 887.5151, calcd for C$_{41}$H$_{79}$N$_2$O$_{16}$S ([M+H]$^+$) 887.5145.

EXAMPLE 8

Compound A-11

Compound A-11. To a solution of compound A-9 (80 mg, 0.0923 mmol) in MeOH (3.0 mL) was added NaOH (1.0 M in H$_2$O, 0.1 mL). The reaction mixture was stirred at RT overnight, and then at 50° C. for 4 h. LC/MS indicated that the starting material was all consumed and the desired product was the only detectable product. The solvent was removed under reduced pressure and the resulting solid was lyophilized to yield compound A-11 (79 mg. 0.092 mmol, 99%) as a sodium salt. m/z: 839.0 ([M+H]$^+$); ESI TOF MS m/z 838.5176, calcd for C$_{41}$H$_{76}$NO$_{16}$ ([M+H]$^+$) 838.5159.

EXAMPLE 9

Intermediate 12

Intermediate 12 (9-dihydro-9-O-(2-aminoethyl)-N-desmethyl-N-isopropyl-erythromycin A) was used in the synthesis of several compounds of this invention.

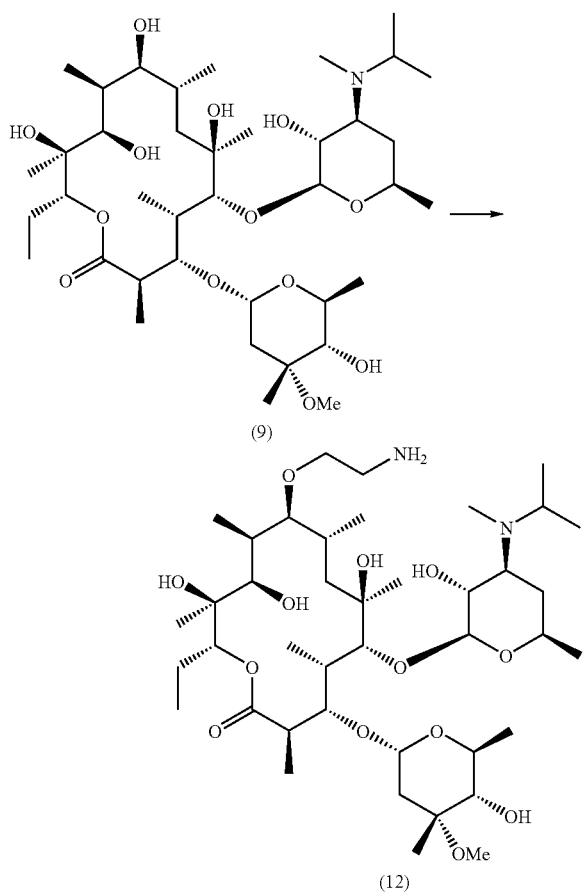

To a solution of intermediate 9 (55 mg, 0.072 mmol) in THF (2.4 mL), was added bromoethylamine hydrobromide (43 mg, 0.209 mmol, 2.9 eq) followed by potassium hydroxide (38 mg, 0.684 mmol, 9.5 eq). The solution was stirred at room temperature for 20 hours before diluting with EtOAc (15 mL) and washing with NaHCO$_3$ (15 mL). The aqueous phase was extracted with EtOAc (3×15 mL) and the combined organic phases were dried (MgSO$_4$) before concentrating under reduced pressure. Column chromatography (silica, 35% acetone-hexane, 1% triethylamine) yielded intermediate 12 (23 mg, 40%) as a white solid; m/z: 808 ([M+H]$^+$), 649.

EXAMPLE 10

Synthesis of Compounds from Intermediate 12

Compound A-30. To a solution of intermediate 12 (50 mg, 0.062 mmol) in CH$_2$Cl$_2$ (1.0 mL) at RT was added pyridine (0.010 mL, 0.124 mmol, 2.0 eq) followed by acetic anhydride (0.007 mL, 0.074 mmol, 1.2 eq). The solution was stirred at RT for 2.5 hours before adding aq. NaHCO$_3$ (15 mL). After extraction with CH$_2$Cl$_2$ (3×15 mL), the organic phases were combined, washed with brine (30 mL), dried (Na$_2$SO$_4$) and concentrated under reduced pressure. Column chromatography (silica, 50% acetone-hexane, 1% triethylamine) yielded a mixture of the desired N-acetyl and 2',N-diacetyl compounds, which were dissolved in methanol (2 mL) and stirred at 50° C. for 3 hours. After cooling, the solvent was concentrated to yield compound A-30 (0.030 g, 57%) as a white solid; m/z: 850 ([M+H]$^+$), ESI TOF MS m/z 849.5682, calcd for C$_{43}$H$_{81}$N$_2$O$_{14}$ ([M+H]$^+$) 849.5682.

Compound A-32. To a solution of intermediate 12 (75 mg, 0.093 mmol) in CH$_2$Cl$_2$ (1.0 mL) at RT was added pyridine (0.015 mL, 0.186 mmol, 2.0 eq) followed by methanesulfonyl chloride (0.009 mL, 0.112 mmol, 1.2 eq). The solution was stirred at RT for 2 hours before adding aq. NaHCO$_3$ (20 mL). After extraction with CH$_2$Cl$_2$ (3×20 mL), the organic phases were combined, dried (MgSO$_4$) and concentrated under reduced pressure. Column chromatography (silica, 30% acetone-hexane, 1% triethylamine) yielded compound A-32 (0.045 mg, 55%) as a white solid; m/z: 886 ([M+H]$^+$), 728; ESI TOF MS m/z 885.5321, calcd for C$_{42}$H$_{81}$N$_2$O$_{15}$S ([M+H]$^+$) 885.5352.

Compound A-54. To a solution of intermediate 12 (0.080 g, 0.099 mmol, 1.0 eq.) in CH$_2$Cl$_2$ (1.0 mL) at RT was added ethyl isocyanate (0.014 g, 0.016 mL, 0.198 mmol, 2.0 eq). The solution was stirred at room temperature for 16 hours before adding further ethyl isocyanate (0.022 g, 0.025 mL, 0.316 mmol, 3.2 eq) and stirring at RT for 4 hours. The solution was poured into aq. NaHCO$_3$ (15 mL). After extraction with CH$_2$Cl$_2$ (3×15 mL), the combined organic phases were dried (MgSO$_4$) and concentrated under reduced pressure. Column chromatography (silica, 35 to 50% acetone-hexane, 1% triethylamine) yielded compound A-54 (0.019 g) as a white solid; m/z: 879 ([M+H]$^+$); ESI TOF MS m/z 878.5954, calcd for C$_{44}$H$_{83}$N$_3$O$_{14}$ ([M+H]$^+$) 878.5948.

Compound A-57. To a solution of intermediate 12 (0.075 g, 0.094 mmol, 1.0 eq) in CH$_2$Cl$_2$ (1.0 mL) was added propyl isothiocyanate (0.014 g, 0.015 mL, 0.141 mmol, 1.5 eq) and the solution was stirred at RT for 18 hr. The solution was poured into NaHCO$_3$ (15 mL) and the organic phases were extracted with CH$_2$Cl$_2$ (3×15 mL). The combined organic phases were dried (MgSO$_4$) and concentrated under reduced pressure. Column chromatography (silica, 50% acetone-hexane, 0-1% triethylamine) yielded compound A-57 (0.032 g, 38%) as a white solid. m/z: 909 ([M+H]$^+$), 751; ESI TOF MS m/z 908.5905, calcd for C$_{45}$H$_{85}$N$_3$O$_{13}$S ([M+H]$^+$) 908.5889.

Compound A-58. To a solution of ethyl-(3-dimethyl)propylcarbodiimide (0.023 g, 0.121 mmol, 1.3 eq) and hydroxybenzotriazole (0.025 g, 0.186 mmol, 2.0 eq) in THF (1.0 eq) at 0° C. was added 5-benzimidazole carboxylic acid (0.018 g, 0.112 mmol, 1.2 eq) The solution was stirred at 0° C. for 15 min before adding intermediate 12 (0.075 g, 0.093 mmol, 1.0 eq). After 1 hour at 0° C., the solution was warmed to RT and stirred for 1 hour. DMF (0.5 mL) was added and the resulting mixture was stirred at RT for 3 hr. After diluting with EtOAc (40 mL), the solution was washed with NaHCO$_3$ (2×30 mL) and brine (30 mL) before drying (Na$_2$SO$_4$) and concentrating under reduced pressure. Column chromatography (silica, 70→90% acetone-hexane, 1% triethylamine) yielded compound A-58 (0.042 g, 48%) as a white solid. m/z: 952 ([M+H]$^+$), 794; ESI TOF MS m/z 951.5898, calcd for C$_{49}$H$_{82}$N$_4$O$_{14}$ ([M+H]$^+$) 951.5900.

Compound A-64. To a solution of intermediate 12 (0.080 g, 0.099 mmol, 1.0 eq) in CH$_2$Cl$_2$ (1.0 mL) was added pyridine (0.016 g, 0.016 mL, 0.198 mmol, 2.0 eq) followed by ethyl chloroformate (0.013 g, 0.011 mL, 0.119 mmol, 1.2 eq). The solution was stirred at RT for 3 hr before adding further ethyl chloroformate (0.013 g, 0.011 mL, 0.119 mmol, 1.2 eq) and stirring for 1 hr. The solution was poured into NaHCO$_3$ (15 mL) and the organic phases were extracted with CH$_2$Cl$_2$ (3×15 mL). The combined organic phases were dried (Na$_2$SO$_4$) and concentrated under reduced pressure. Column chromatography (silica, 50% acetone-hexane, 1% Et$_3$N) yielded compound A-64 (0.030 g, 34%) as a white solid; m/z: 880 ([M+H]$^+$); ESI TOF MS m/z 879.5796, calcd for C$_{44}$H$_{82}$N$_2$O$_{15}$ ([M+H]$^+$) 879.5788.

Compound A-65. A similar method as that for compound A-64 was used, with methyl chloroformate replacing ethyl chloroformate. m/z: 866 ([M+H]$^+$); ESI TOF MS m/z 865.5630, calcd for C$_{43}$H$_{80}$N$_2$O$_{15}$ ([M+H]$^+$) 856.5632.

Compound A-67. A similar method as that for compound A-57 was used, with ethyl isothiocyanate replacing propyl isothiocyanate. m/z: 895 ([M+H]$^+$); ESI TOF MS m/z 894.5724, calcd for $C_{44}H_{83}N_3O_{13}S$ ([M+H]$^+$) 894.5719.

Compound A-78. To a solution of intermediate 12 (0.150 g, 0.186 mmol, 1.0 eq) in DMF (2.0 mL) at 0° C. was added dimethylaminopropylethylcarbodiimide (0.079 g, 0.409 mmol, 2.2 eq) and hydroxybenzotriazole (0.050 g, 0.372 mmol, 2.0 eq) followed by formic acid (0.017 g, 0.014 mL, 0.372 mmol, 2.0 eq). The solution was stirred at 0° C. for 30 minutes and room temperature for 3 hours before partitioning between EtOAc (25 mL), and NaHCO$_3$ (25 mL). The aqueous phase was extracted with EtOAc (25 mL) and the combined organics washed with water (35 mL), NaHCO$_3$ (35 mL) and brine (40 mL) before drying (Na$_2$SO$_4$) and concentrating under reduced pressure. Column chromatography (silica, 40% acetone-hexane, 1% triethylamine) yielded compound A-78 (0.072 g, 46%) as a white solid. m/z: 836 ([M+H]$^+$), 678; ESI TOF MS m/z 835.5501, calcd for $C_{42}H_{78}N_2O_{14}$ ([M+H]$^+$) 835.5526.

EXAMPLE 11

Intermediate 15

Intermediate 15 was used in the synthesis of several compounds of this invention.

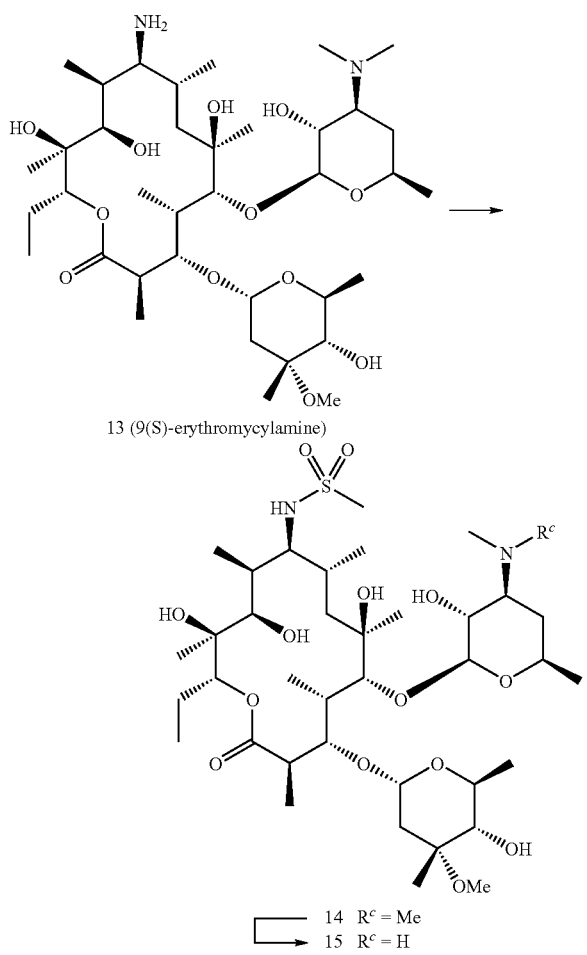

To a solution of 9(S)-erythromycylamine 13 (15.8 g, 21.5 mmol; see, e.g., Massey et al., *J. Med. Chem.*, 1974, 17 (1), 105-107) in CH$_2$Cl$_2$ (60 mL) was added diisopropylethylamine (14.8 mL, 85.0 mmol), followed by methanesulfonic anhydride (6.45 g, 37.0 mmol) in CH$_2$Cl$_2$ (35 mL) at −10° C. in 1 h, and stirring was continued for another 1.5 hour at that temperature. The reaction mixture was quenched by adding saturated NaHCO$_3$ (100 mL) and Na$_2$CO$_3$ (10% in H$_2$O, 20 mL). The resultant mixture was stirred for 10 min at RT. The organic layer was separated and the aqueous layer was extracted with EtOAc (2×20 mL). The combined organic layers were dried over MgSO$_4$/K$_2$CO$_3$, filtered through a thin pad of K$_2$CO$_3$, and concentrated under reduced pressure. The residue was purified by column chromatography (5% to 70% acetone in hexanes, 1% triethylamine) to yield 9.9 g (12.2 mmol, 56%) of pure compound 14 as a white solid. ESI TOF MS m/z 813.4770, calcd for $C_{38}H_{73}N_2O_{14}S$ ([M+H]$^+$) 813.4740.

To a stirred solution of compound 14 (86.8 mg, 0.107 mmol) and sodium acetate (43.9 mg, 0.535 mmol, 5.0 eq.) in MeOH/H$_2$O (4:1, 2 mL) was added iodine (29.8 mg, 0.117 mmol, 1.1 eq.) at 50° C. Then 0.1 N NaOH solution (1.17 mL, 0.117 mmol, 1.1 eq.) was added drop-wise over 1 h. Stirring was continued for 2 h at the same temperature. NaOH (0.1 mL, 0.1N) and I$_2$ (3 mg) were added and the reaction mixture was stirred for 1 hour. The reaction mixture was concentrated to about 200 µL and diluted with CH$_2$Cl$_2$ (10 mL) and saturated NaHCO$_3$ (5 mL). The aqueous layer was extracted with CH$_2$Cl$_2$ (3×5 mL). The combined organic phases were washed with diluted Na$_2$S$_2$O$_3$ (5 mL), H$_2$O (5 mL) and dried over MgSO$_4$. The solution was filtered and the solvent was removed under reduced pressure. Purification by column chromatography (0% to 5% MeOH in CH$_2$Cl$_2$, 2% triethylamine) yielded intermediate 15 as a white solid (70 mg, 84%).

EXAMPLE 12

Synthesis of Compounds from Intermediate 15

Compound A-35. To a solution of intermediate 15 (35 mg, 0.044 mmol) in CH$_3$CN (400 µL) was added diisopropylethylamine (76.3 µL, 0.44 mmol, 10.0 eq) and 2-iodopropane (65.7 µL, 0.66 mmol, 15.0 eq). The solvent was removed under reduced pressure and the residue was purified with column chromatography (5% to 70% acetone in hexanes, 1% triethylamine) to yield compound A-35 (24 mg, 65%). m/z: 842.0 ([M+H]$^+$); ESI TOF MS m/z 841.5093, calcd for $C_{40}H_{77}N_2O_{14}S$ ([M+H]$^+$) 841.5090.

Compound A-36. A similar method as that for compound A-35 was used, but with 2-iodoethanol as the alkylating agent. m/z: 844.0 ([M+H]$^+$); ESI TOF MS m/z 843.4894, calcd for $C_{40}H_{75}N_2O_{15}S$ ([M+H]$^+$) 843.3883.

Compound A-37. To a solution of intermediate 15 (120 mg, 0.15 mmol) in CH$_3$OH (1.2 mL) was added 2,2-dimethyloxirane (133 µL, 1.5 mmol, 10 eq). The reaction mixture was stirred at 50° C. for overnight, and then concentrated under reduced pressure. The residue was purified with column chromatography (5% to 50% acetone in hexanes, 1% triethylamine) to yield compound A-37 (73 mg, 54%) of as a white solid. m/z: 872.0 ([M+H]$^+$); ESI TOF MS m/z 871.5171, calcd for $C_{41}H_{79}N_2O_{15}S$ ([M+H]$^+$) 871.5196.

Compound A-38. A similar method as that for compound A-35 was used, but with 1-iodo-2-methylpropane as the alkylating agent. m/z: 856.0 ([M+H]$^+$); ESI TOF MS m/z 855.5186, calcd for $C_{41}H_{79}N_2O_{14}S$ ([M+H]$^+$) 855.5247.

Compound A-39. To a solution of intermediate 13 (240 mg, 0.30 mmol.), NaCNBH$_3$ (43.4 mg, 0.69 mmol, 2.3 eq) and acetic acid (69 µL, 1.2 mmol, 4.0 eq) in MeOH (2.0 mL) was added cyclobutanone (45 µL, 0.6 mmol, 2.0 eq). The reaction mixture was stirred at RT overnight and diluted with EtOAc (30 mL), Na$_2$CO$_3$ (10%, 5 mL) and saturated NaHCO$_3$ (10 mL), brine (10 mL). The aqueous layer was extracted with EtOAc (2×10 mL). The combined organic phases were dried over Na$_2$SO$_4$, filtered and concentrated. The residue was purified by column chromatography (5% to 50% acetone in hexanes, 1% triethylamine) to yield compound A-39 as a white solid (106 mg, 42%). m/z: 854.0([M+H]$^+$); ESI TOF MS m/z 853.5090, calcd for C$_{41}$H$_{77}$N$_2$O$_{14}$S ([M+H]$^+$) 853.5090.

EXAMPLE 13

Synthesis of Intermediate 19

Intermediate 19, the 4"-deoxy counterpart of intermediate 9, was synthesized from 4"-deoxyerythromycin A (16), using procedures analogous to those used for the preparation of intermediate 9: m/z: 779 ([M+H]$^+$), 621; ESI TOF MS m/z 778.5345, calcd for C$_{40}$H$_{76}$NO$_{13}$ ([M+H]$^+$) 778.5311.

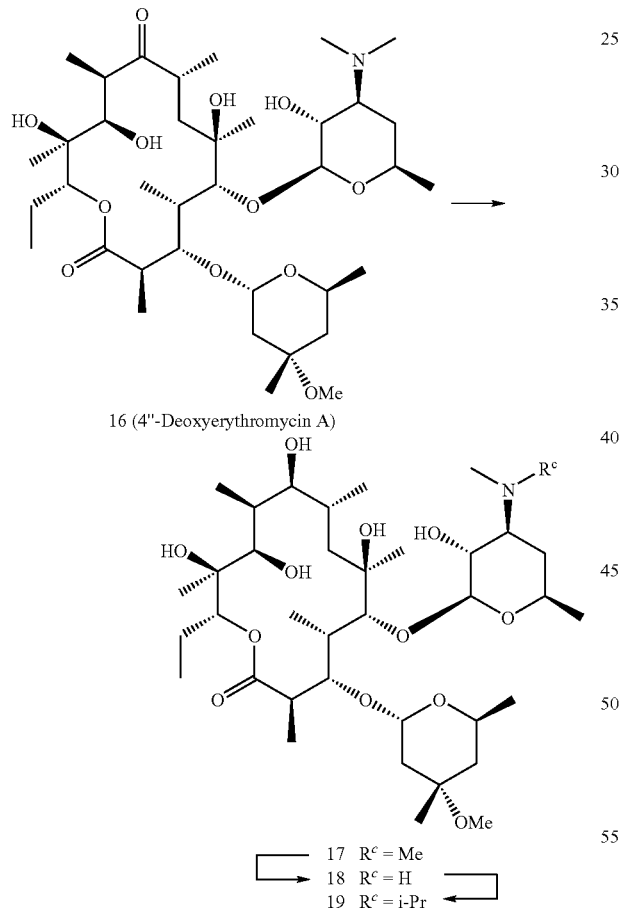

16 (4"-Deoxyerythromycin A)

17 R$^c$ = Me
18 R$^c$ = H
19 R$^c$ = i-Pr

EXAMPLE 14

Synthesis of Compounds from Intermediate 19

Compound A-60. A similar method as that for compound A-12 was used, but with intermediate 19 as starting material, and with N,N-dimethyl bromoacetamide as alkylating agent instead of bromoacetamide. m/z: 833.6 ([M+H]$^+$).

Compound A-61. A similar method as that for compound A-12 was used, but with intermediate 19 as starting material and with N-methyl bromoacetamide as the alkylating agent instead of bromoacetamide. m/z: 819.6 ([M+H]$^+$).

Compound A-68. A similar method as that for compound A-12 was used, but with intermediate 19 as starting material. m/z: 806.0 ([M+H]$^+$), ESI TOF MS m/z 805.5410, calcd for C$_{41}$H$_{77}$N$_2$O$_{13}$ ([M+H]$^+$) 805.5420.

EXAMPLE 15

Synthesis of Intermediate 23

Intermediate 23, the erythromycin B counterpart of intermediate 9, was synthesized from erythromycin B (20), using procedures analogous to those used for the preparation of intermediate 9: m/z: 748.5 ([M+H]$^+$). ESI TOF MS m/z 748.5225, calcd for C$_{39}$H$_{74}$NO$_{12}$ ([M+H]$^+$) 748.5206.

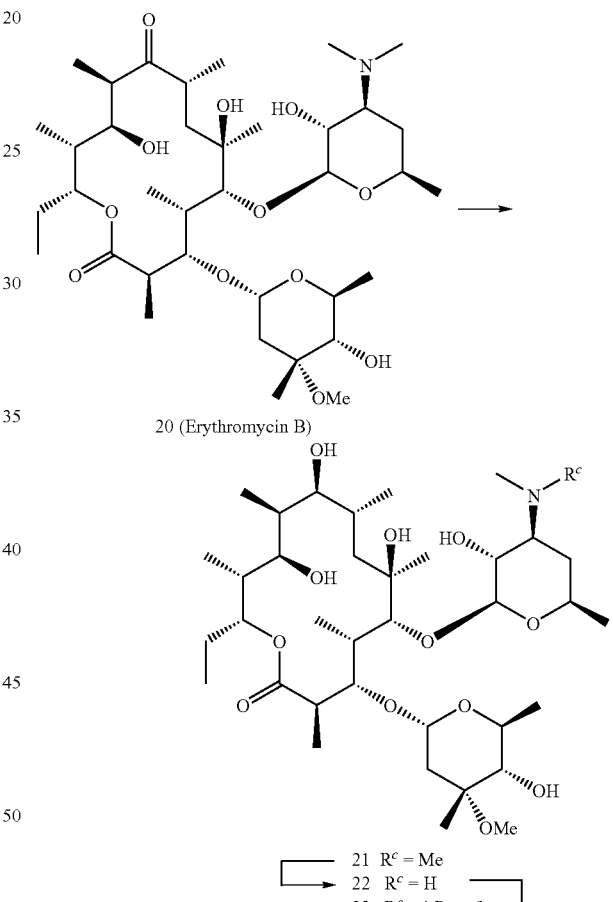

20 (Erythromycin B)

21 R$^c$ = Me
22 R$^c$ = H
23 R$^c$ = i-Pr

EXAMPLE 16

Synthesis of Compounds from Intermediate 23

Compound A-71. A solution of potassium tert-butoxide (1 M in THF, 0.98 mL, 0.98 mmol) was added to solution of intermediate 23 (490 mg, 0.66 mmol) in anhydrous dimethoxyethane (6 mL) under an inert atmosphere and stirred at room temperature for 10 min. N-Methylbromoacetamide (120 mg, 0.79 mmol) was added and the reaction mixture stirred for 30 min. TLC analysis indicated complete consumption of the starting material and the excess reagents were quenched by addition of saturated NaHCO$_3$ solution and the mixture was extracted with EtOAc. The combined organic layers were dried with Mg$_2$SO$_4$ and concentrated under reduced pressure. Flash chromatography using hexane and acetone with 2% Et$_3$N gave the desired product. ESI TOF MS m/z 819.5572, calcd for C$_{42}$H$_{79}$N$_2$O$_{13}$ ([M+H]$^+$) 819.5577. $^{13}$C NMR (CDCl$_3$). 177.6, 170.7, 102.2, 94.8, 93.4, 84.8, 77.7, 77.4, 75.7, 74.6, 72.8(2), 70.7, 70.0, 69.4, 65.6, 62.2, 52.6, 49.3, 43.7, 43.1, 38.8, 34.7, 32.8(2), 31.0, 25.5, 24.4, 21.5, 21.2, 21.1, 20.4, 19.9, 17.6, 12.7, 11.7, 9.8, 9.7, 9.2.

Compound A-72. A similar method as that for compound A-12 was used, but with intermediate 23 as the starting material and with N,N-dimethylbromoacetamide as the alkylating agent instead of bromoacetamide. ESI TOF MS m/z 833.5699, calcd for C$_{43}$H$_{81}$N$_2$O$_{13}$ ([M+H]$^+$) 833.5733.

Compound A-75. A similar method as that for compound A-12 was used, but with intermediate 23 as starting material and with N,N-dimethylcarbamoy chloride as the alkylating agent instead of bromoacetamide. ESI TOF MS m/z 819.5548, calcd for C$_{42}$H$_{79}$N$_2$O$_{13}$ ([M+H]$^+$) 819.5577.

EXAMPLE 17

Compounds with R$^F$ Equals Methyl

Intermediate 27, the 6-O-methyl analog of intermediate 9, was prepared from compound 24 (6-O-methyl erythromycin A, also known as clarithromycin) using procedures analogous to those for making intermediate 9: m/z: 779 ([M+H]$^+$), 621; ESI TOF MS m/z 778.5345, calcd for C$_{40}$H$_{76}$NO$_{13}$ ([M+H]$^+$) 778.5311.

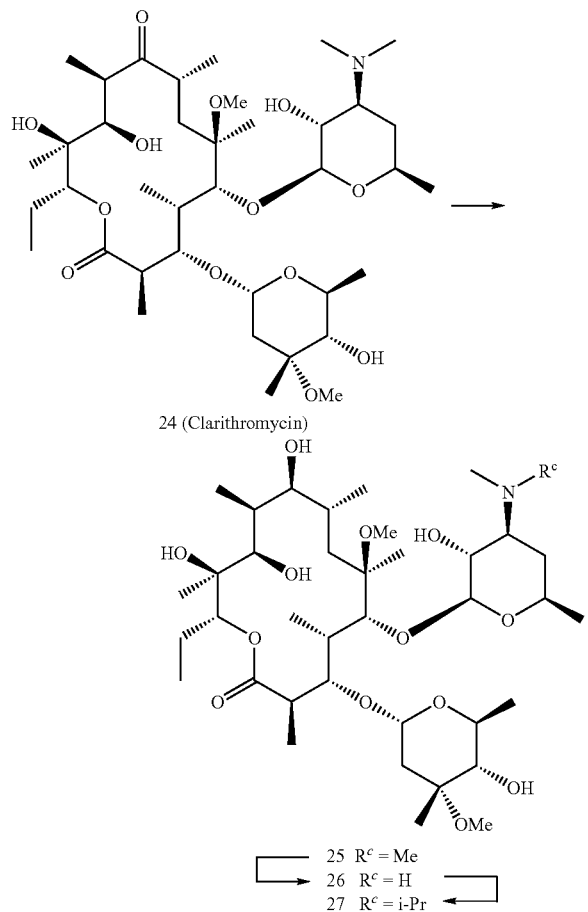

24 (Clarithromycin)

25 R$^c$ = Me
26 R$^c$ = H
27 R$^c$ = i-Pr

Compound A-66. A similar method as that for compound A-12 was used, but with intermediate 27 as the starting material and with N-methyl bromoacetamide as alkylating agent instead of bromoacetamide. m/z: 850.0 ([M+H]$^+$),]$^+$); ESI TOF MS m/z 849.5710, calcd for C$_{43}$H$_{81}$N$_2$O$_{14}$ ([M+H]$^+$) 849.5682.

EXAMPLE 18

Synthesis of Other Compounds

Compound A-40. A similar method as that for making intermediate 15 was used to make the ethanesulfonamide, which was then demethylated and realkylated with isopropyl iodide as described above in connection with compound A-38 to give compound A40. m/z: 856.0([M+H]$^+$).

Compound A-41. A similar method as that for intermediate 15 was used to make the cyclopropanesulfonamide, which was then demethylated and realkylated with isopropyl iodide as described above to give compound A-41. m/z: 868.0([M+H]$^+$).

Compound A-42. Same method as that for compound A41 was used, but the desmethyl intermediate was reacted with cyclobutanone under reductive amination conditions as described above to give compound A-42. m/z: 880.0([M+H]$^+$).

Compound A-43. Similar method as that for compound A-39 was used to make to the trifuoromethanesulfonamide, which was then demethyled and realkylated with isopropyl iodide as described above to give compound A-43. m/z: 896.0 ([M+H]$^+$)

Compound A-44. Similar method as that for compound A-40 was used, but with dimethylsulfamoyl chloride. m/z: 872.0 ([M+H]$^+$); ESI TOF MS m/z 871.5218, calcd for C$_{41}$H$_{79}$N$_2$O$_{15}$S ([M+H]$^+$) 871.5196.

Compound A-56. To a solution of compound A-22 (62 mg, 0.074 mmol, 1.0 eq) in CH$_3$OH (1 mL) was added NaOH (1.0 N, 0.078 mL, 1.05 eq). The reaction mixture was stirred at RT for 2 days, then was concentrated and the residue was lyophilized with tBuOH/H$_2$O (93:7) to provide compound A-56 (60 mg, 0.071 mmol, 96%) as the sodium salt. m/z: 823.0 ([M+H]$^+$); ESI TOF MS m/z 822.5214, calcd for C$_{41}$H$_{75}$NO$_{15}$ ([M+H]$^+$) 822.5223.

Those skilled in the art will appreciate that the foregoing synthetic techniques can be applied, mutatis mutandis, to make other compounds of this invention, including those wherein R$^C$, R$^D$, R$^E$, and R$^F$ are other than OH, Me, OH, and H, respectively, using alternative known and/or commercially available precursor materials. Compounds in which R$^F$ is Me can be made from clarithromycin (6-O-methylerythromycin A, Biaxin™; Watanabe et al., U.S. Pat. No. 4,331,803 (1982)). Compounds wherein R$^C$ and R$^D$ are other than OH and Me, respectively, can be made using as precursors erythromycins B, C, or D. Compounds in which R$^E$ is H can be made by removing the 4"-OH group from an erythromycin, for example as taught in Lartey et al., U.S. Pat. No. 5,578,579 (1996).

EXAMPLE 19

Tissue Based Assay for Motilin Agonist Potency

The motilin agonist potencies of compounds of this invention were evaluated using a tissue based assay, using rabbit duodenum tissue-based contractility assay, generally following the procedure of Depoortere et al., *J. Gastrointestinal Motility*, 1, 150-159 (1989), the disclosure of which is incorporated herein by reference. Briefly, this method measures the ability of a compound to induce contractions in rabbit duodenal tissue, a motilin receptor-bearing tissue contractilely responsive to motilin.

Strips of rabbit duodenum were tested and qualified for use in the assay by as follows. Segments of rabbit duodenum, 20-30 cm distal to the pylorus were split longitudinally. The mucosa was removed and 2×2×15 mm strips of longitudinal smooth muscle were sliced from the segments. The strips were bathed in oxygenated Krebs solution at 37° C., with 1.5 g of tension, and contractions measured auxotonically. Strips exhibiting strong, regular phasic activity (amplitude 0.3 g, FFT peak at 0.3-0.4 Hz, >3-fold stronger than other peaks), and prompt, reproducible responses to 1 uM carbachol ("CCH") (peak contraction in <30 s, >3× phasic amplitude) were qualified for use in the assay; strips not meeting the foregoing criteria were discarded.

The carbachol was then washed away by changing the organ bath buffer twice. The strips were washed again 20±5 minutes following the carbachol contraction. Following this last wash a dose response study was initiated within 10±5 min. Each compound tested was dissolved in dimethylsulfoxide (DMSO) to a final concentration of 10 mM. A series of seven 10× serial dilutions in water was prepared, so that the concentration of the seventh serial dilution was $1.0 \times 10^{-6}$ mM. The first through fifth serial dilutions of the compound were applied, starting with 200 µL of the most dilute solution. After each application, there was a wait of 2±0.5 min, until the response was stable, before the application of the next dose (the next higher concentration serial dilution). The dose was increased in 10-fold increments until a small response was observed. Subsequent doses were the increased in 2- to 5-fold increments, until the maximum response was obtained. At 2±0.5 min after the last drug addition, the strips were dosed with 1 µM carbachol.

The $EC_{50}$ (concentration producing a half-maximal effect) was calculated as follows. The basal tension was subtracted from the compound-induced tension for each reading. The data points were normalized against the response obtained from 1 µM carbachol at the end of the experiment. The concentration of compound was plotted against the response and fitted to the following equation:

$$R = (R_{max} \cdot C)/(EC_{50} + C)$$

where R is the contraction response, $R_{max}$ is the maximal contraction response, and C is the concentration of compound. Both R and $R_{max}$ are expressed as a fraction of the 1 µM carbachol contraction and range from 0 to 1. Results are reported in Table B, below.

Optionally an $EC_{90}$ (concentration producing 90% of the maximal effect) could be estimated and verified as follows: $EC_{90}$ was initially approximated as ten times $EC_{50}$. The accuracy of this approximation was then verified by a dose response curve. Qualified duodenum strips were dosed at $0.25 \cdot EC_{90}$. After a maximal response was obtained (2±0.5 min), the dose was increased four-fold. After 2±0.5 min, the strips were dosed with 1 µM carbachol. The difference between the two doses should be in the range of 10-20%. A second set of qualified duodenum strips was dosed at $EC_{90}$. After a maximal response was obtained (2±0.5 min), the dose was increased two-fold. After 2±0.5 min, the strips were dosed with 1 µM carbachol. There should be less than 10% difference between the two doses.

Thus, compounds of this invention can be used to induce the contraction of motilin receptor bearing tissue that is contractilely responsive to motilin. The induction of such contractions can have beneficial effects in stimulating GI motility. The tissue can be mammalian tissue such as rabbit or human tissue, especially GI tissue.

EXAMPLE 20

Evaluation of Antibacterial Activity

The antibacterial activities of compounds of this invention were evaluated by measuring their minimum inhibitory concentrations (MICs) against *Streptococcus pneumoniae* ATCC 6301 (an erythromycin A sensitive strain), using serial dilutions on 96-well microtiter plates. Desirably, the compounds have low antibacterial activity. Results are reported in Table B, below.

Table B below summarizes data for compounds of this invention. Comparative data for erythromycin A, ABT-229, GM-611, and KC-11458 are also presented. The last three compounds are developmental motilides from Abbott Laboratories, Chugai, and Solvay, respectively.

TABLE B

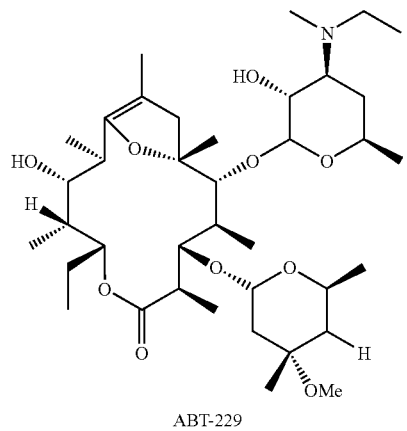

ABT-229

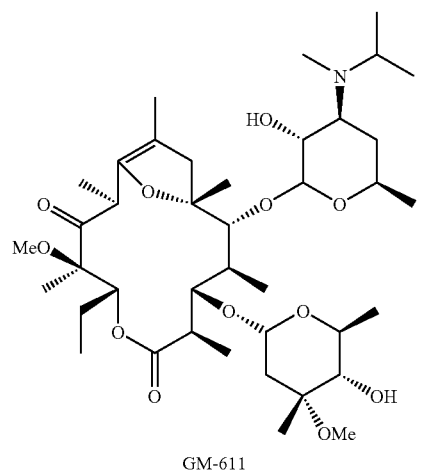

GM-611

TABLE B-continued

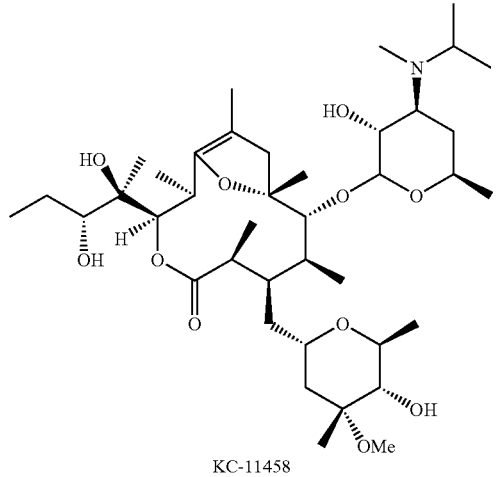

KC-11458

| Compound | Motilin Receptor Agonist Activity (EC$_{50}$, nM) | Antibacterial Activity (MIC, μg/mL) |
|---|---|---|
| Erythromycin A | 1,200 | 0.0025 |
| ABT-229 | 7 | 64 |
| GM-611 | 11 | 128 |
| KC-11458 | 45 | >128 |
| A-1 | 66 | — |
| A-2 | 140 | 64 |
| A-3 | 54 | 64 |
| A-4 | — | 128 |
| A-5 | 320 | 64 |
| A-6 | 1,100 | 128 |
| A-7 | 210 | >128 |
| A-8 | 88 | 128 |
| A-9 | 430 | >128 |
| A-10 | 680 | >128 |
| A-11 | 740 | >128 |
| A-12 | 52 | 64 |
| A-13 | 220 | >128 |
| A-14 | 104 | >128 |
| A-15 | 660 | 64 |
| A-16 | 2,900 | >128 |
| A-17 | 650 | 64 |
| A-18 | 310 | 128 |
| A-19 | 91 | 128 |
| A-20 | 490 | 128 |
| A-21 | 58 | 64 |
| A-22 | 140 | 128 |
| A-23 | 560 | >128 |
| A-24 | 860 | >128 |
| A-25 | 1,200 | >128 |
| A-26 | 480 | 128 |
| A-27 | 110 | 128 |
| A-28 | >420 | 128 |
| A-29 | 290 | 128 |
| A-30 | 48 | >128 |
| A-31 | 67 | >128 |
| A-32 | 240 | >128 |
| A-33 | 120 | >128 |
| A-34 | 120 | 128 |
| A-35 | 190 | 64 |
| A-36 | 66 | 32 |
| A-37 | 52 | 64 |
| A-38 | 140 | 128 |
| A-39 | 280 | >128 |
| A-40 | 350 | 128 |
| A-41 | 170 | 128 |
| A-42 | 340 | >128 |
| A-43 | 330 | 64 |
| A-44 | 91 | 128 |
| A-45 | 28 | 128 |
| A-46 | 31 | 128 |
| A-47 | 220 | — |
| A-48 | 140 | 64 |

TABLE B-continued

| A-49 | 140 | 128 |
|---|---|---|
| A-50 | 170 | >128 |
| A-51 | 510 | >128 |
| A-52 | 160 | 128 |
| A-53 | 140 | 128 |
| A-54 | 100 | >128 |
| A-55 | 54 | >128 |
| A-56 | 150 | 128 |
| A-57 | 210 | 128 |
| A-58 | 37 | 128 |
| A-59 | 79 | 128 |
| A-60 | 190 | 128 |
| A-61 | 17 | 128 |
| A-62 | 63 | 128 |
| A-63 | 50 | 128 |
| A-64 | 100 | 64 |
| A-65 | 130 | 128 |
| A-66 | 400 | — |
| A-67 | 220 | >128 |
| A-68 | 36 | >129 |
| A-69 | 92 | — |
| A-70 | 60 | 128 |
| A-71 | 90 | >128 |
| A-72 | 270 | >128 |
| A-73 | 84 | 128 |
| A-74 | 270 | 128 |
| A-75 | 290 | >128 |
| A-76 | 150 | 128 |
| A-77 | 25 | >128 |
| A-78 | 31 | — |
| A-79 | 400 | — |

EXAMPLE 21

Chronic Dosing Model for Evaluating Tachyphylaxis

This example describes how tachyphylaxis (decrement in response after an initial administration; in effect a desensitization to the agonist effect of the compound) of compounds of this invention can be evaluated.

Rabbit duodenum strips are qualified as described above and dosed with test compound at its EC$_{90}$ concentration. The contraction is recorded. When peak contractile force is reached, carbachol (1 μM) is added, and any further contraction is recorded. The resulting contraction are expressed as a fraction of the 1 μM carbachol contraction. The test compound and carbachol are washed away by changing the bath solution twice. The procedure is repeated at 30, 60, and 90 min following the initial dosing. Tachyphylaxis is quantitated as the percentage of the initial contraction retained after the fourth dose of the compound being tested. A compound exhibiting low tachyphylaxis will have a high value.

Tachyphylaxis=100%×(Contraction after 4th dose)/(Contraction after initial dose)

EXAMPLE 22 hERG Channel Inhibition

The pro-arrhythmic effects of erythromycin and related compounds have been attributed to their inhibition of the HERG (human ether-a-go-go related gene) potassium channel. The hERG channel inhibitory effects of compounds of this invention can be evaluated using the technique reported in Stanat et al., *Mol. Cellular Biochem.*, 2003, 254, 1-7, "Characterization of the Inhibitory Effects of Erythromycin and Clarithromycin on the HERG Potassium Channel". Inhibition may be expressed as % inhibition at 30 µM concentration of the compound being tested. Desirably, compounds have a low % inhibition.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various descriptions herein relate to specific embodiments of the invention, it is to be understood that where a specific feature is disclosed in the context of a particular embodiment, such feature can also be used, to the extent appropriate, in the context of another embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A compound having a structure represented by formula (I)

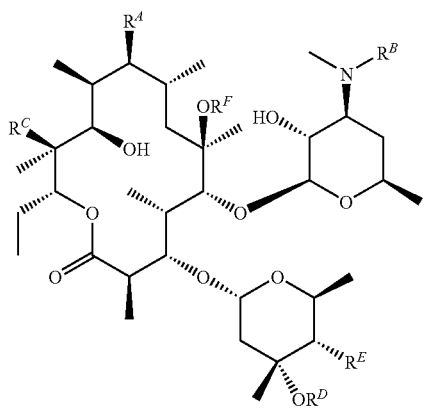

and the pharmaceutically acceptable salts, solvates, and hydrates thereof,
wherein
(A) $R^A$ is
  (i) $OR^1$;
  (ii) $O(CH_2)_mC(=O)R^2$;
  (iii) $OC(=O)R^4$;
  (iv) $OS(O_2)N(R^3R^{3A})$;
  (v) $O(CH_2)_nNHR^5$;
  (vi) $N(H)S(O_2)R^6$;
  (vii) $OCH_2CH_2OCH_2CH_2C(=O)R^2$; or
  (viii) $OCH_2CH_2OCH_2CH_2NHR^5$;
(B) $R^B$ is selected from the group consisting of $C_2$-$C_4$ alkyl, $C_3$-$C_4$ alkenyl, or $C_3$-$C_4$ alkynyl, 3- or 4-membered cycloaliphatic, and 3- or 4-membered heterocycloaliphatic, each member of the group being optionally substituted with one or more substituents selected from the group consisting of OH, CN, and halogen;
(C) $R^C$ is H or OH;
(D) $R^D$ is H or Me;
(E) $R^E$ is H or OH; and
(F) $R^F$ is H or Me;

wherein
$R^1$ is $C_1$-$C_4$ alkyl, which $C_1$-$C_4$ alkyl is optionally substituted with OH, CN, $O(C_1$-$C_3$ alkyl), halogen, aryl, cycloaliphatic, heteroaryl, or heterocycloaliphatic, said aryl, cycloaliphatic, heteroaryl and heterocycloaliphatic moieties being optionally substituted with $C_1$-$C_4$ alkyl;
$R^2$ is $OR^3$, $N(R^3R^{3A})$, $C_1$-$C_4$ alkyl, $(CH_2)_nOH$, or $C_2$-$C_4$ haloalkyl;
$R^3$ is H, $C_1$-$C_4$ alkyl, or $(CH_2)_nOH$;
$R^{3A}$ is H, $C_1$-$C_4$ alkyl, $(CH_2)_nOH$, $(CH_2)_nO(C_1$-$C_2$ alkyl), $C_2$-$C_4$ haloalkyl, $C_1$-$C_4$ alkyl(aryl), $C_1$-$C_4$ alkyl(heteroaryl), $O(C_1$-$C_4$ alkyl), heteroaryl, or

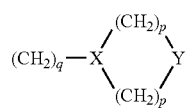

wherein
X is N or CH;
Y is O, S, NH, $N(C_1$-$C_3$ alkyl), $CH_2$, or a bond;
each p is (i) independently 1 or 2 when X is $CH_2$; (ii) 2 when X is N and Y is other than $CH_2$ or a bond; and (iii) independently 1 or 2 when X is N and Y is $CH_2$ or a bond; and
q is (i) 0, 1, 2, or 3 when X is CH and (ii) 2 or 3 when X is N;
$R^4$ is $N(R^3R^{3A})$ or $C_1$-$C_4$ alkyl;
$R^5$ is $S(O_2)(C_1$-$C_4$ alkyl), $C(=O)(C_1$-$C_4$ alkyl), $C(=O)$ aryl, $C(=O)$(heteroaryl), $C(=O)H$, or $C(=W)NH(C_1$-$C_4$ alkyl), where W is O or S;
$R^6$ is $C_1$-$C_4$ alkyl, cyclobutyl, cyclopropyl, $CF_3$, or $N(R^3R^{3A})$;
m is 1, 2, 3, 4, 5, or 6; and
n is, independently for each occurrence thereof, 2, 3 or 4.

2. A compound according to claim 1, having a structure represented by formula (Ia):

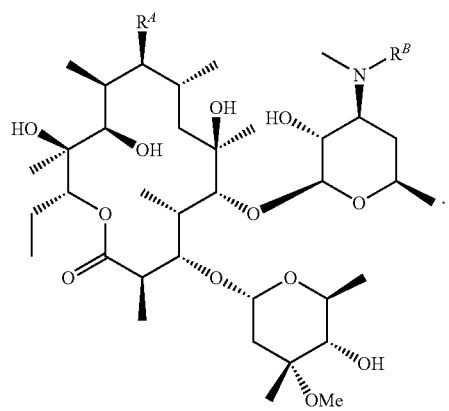

3. A compound according to claim 1, wherein $R^A$ is selected from the group consisting of:

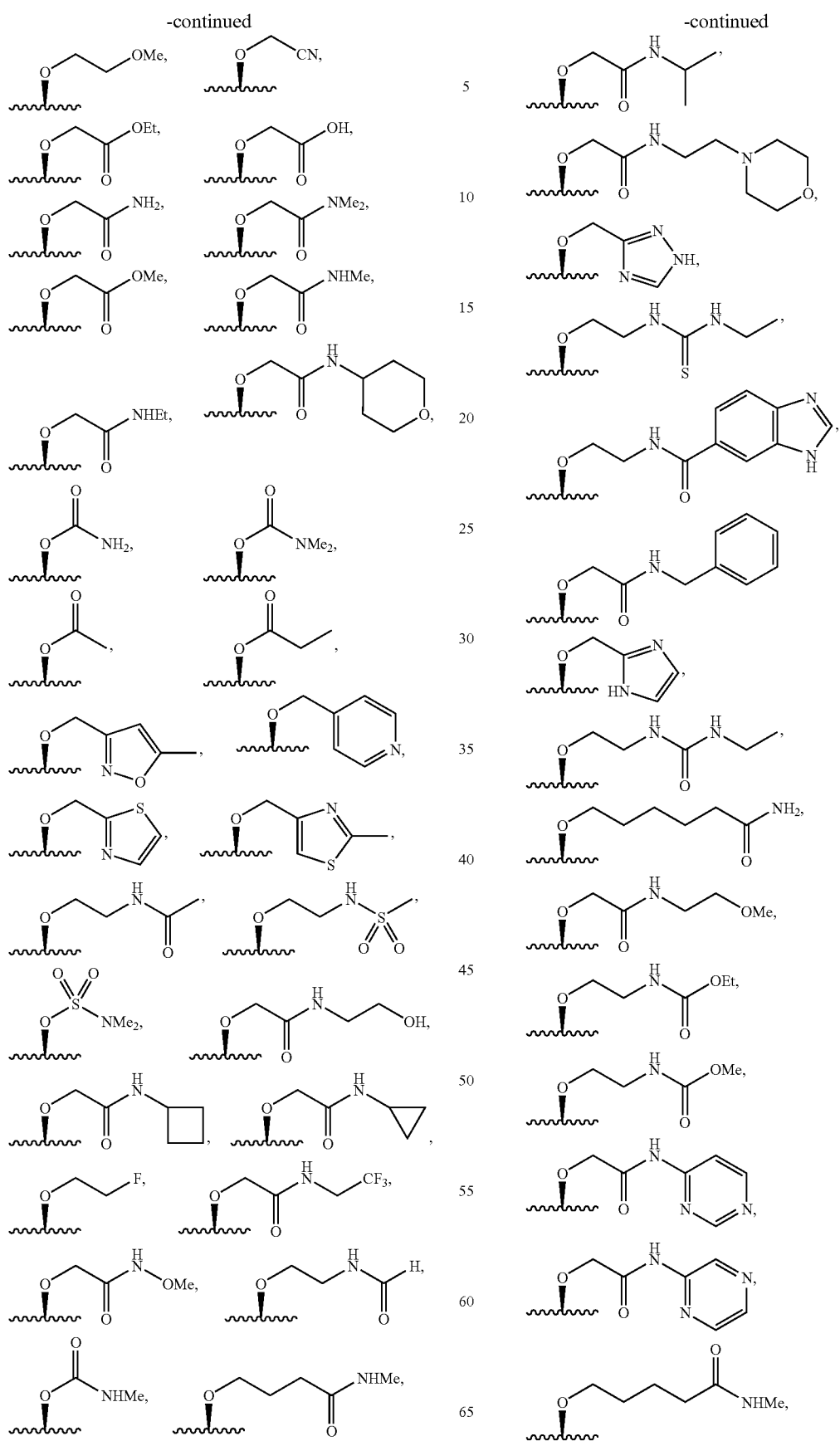

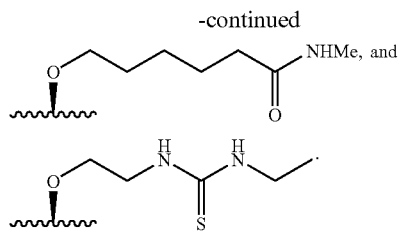

4. A compound according to claim 1, wherein $R^A$ is selected from the group consisting of:

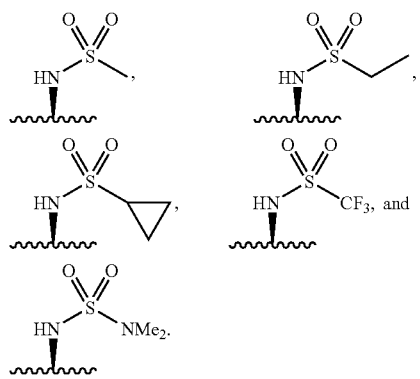

5. A compound according to claim 1, wherein $R^A$ is selected from the group consisting of:

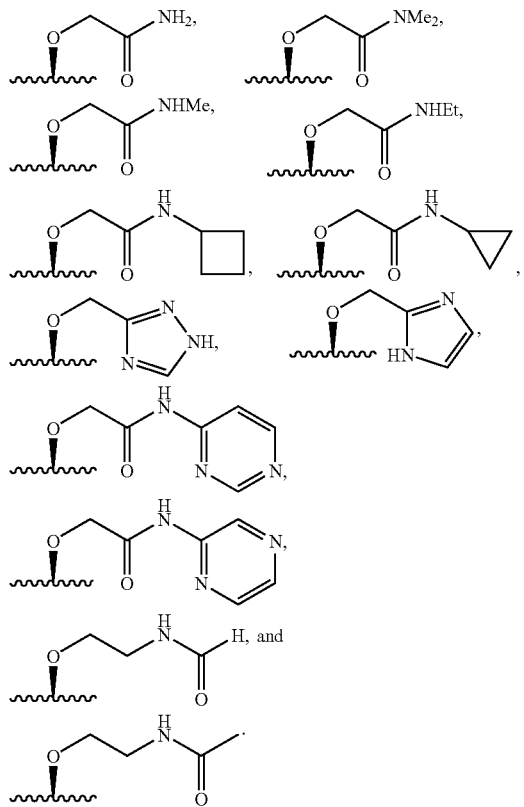

6. A compound according to claim 5, wherein $R^B$ equals

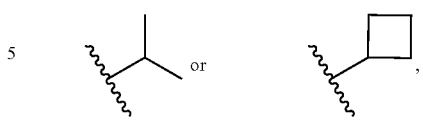

$R^C$ equals H or OH, $R^D$ equals Me, $R^E$ equals H or OH, and $R^F$ equals H or Me.

7. A compound according to claim 2, having a structure represented by formula Ib, Ic, Ic', Ic'', Ic''', Id, Id', Ie, If, Ig, Ih or Ii:

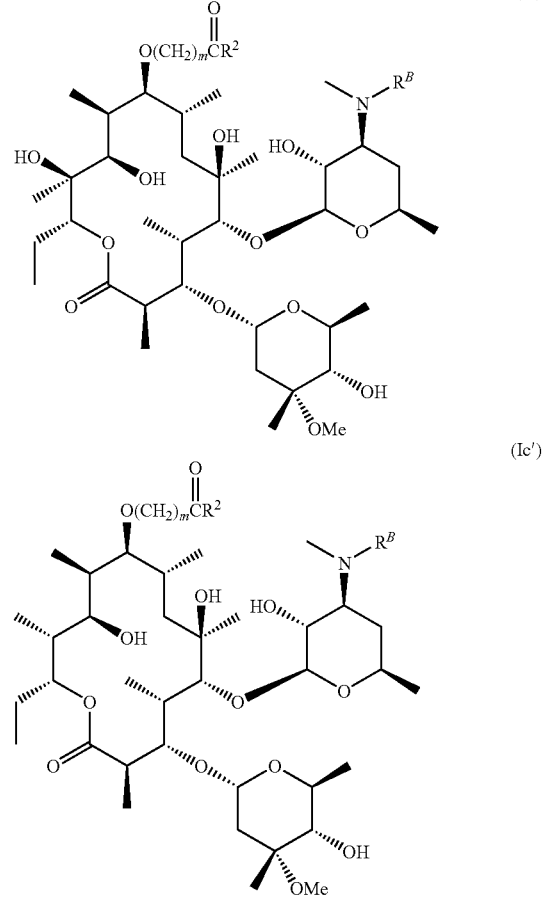

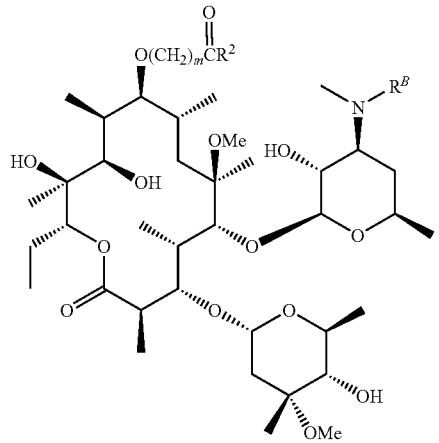
(Ic″)
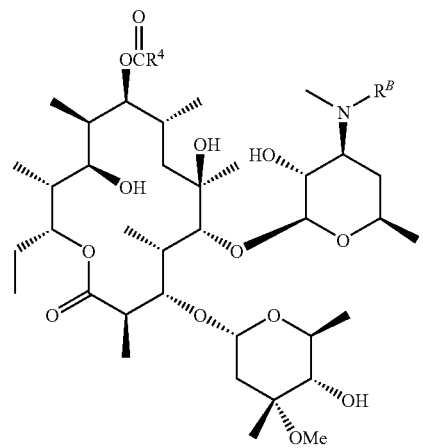
(Id′)
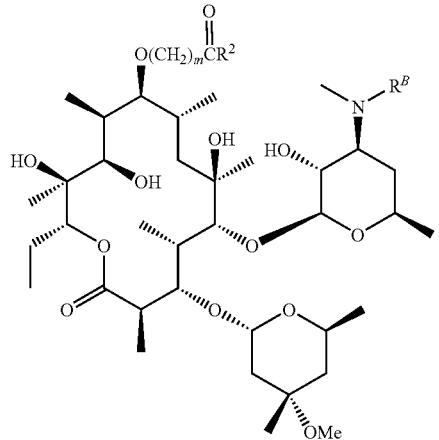
(Ic‴)
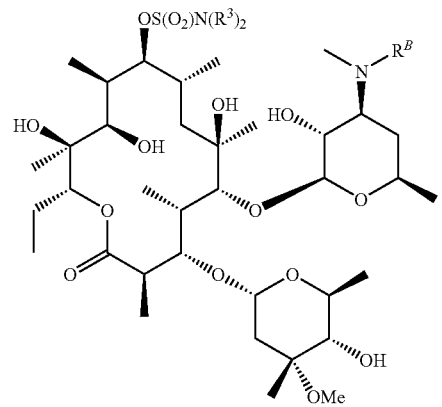
(Ie)
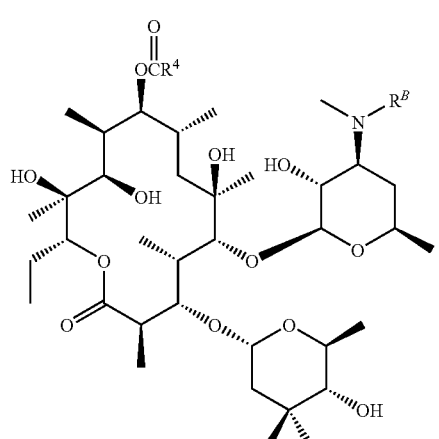
(Id)
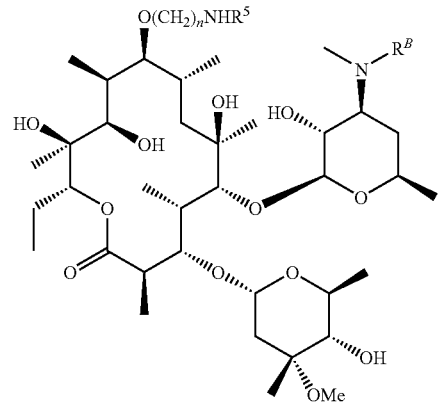
(If)

-continued
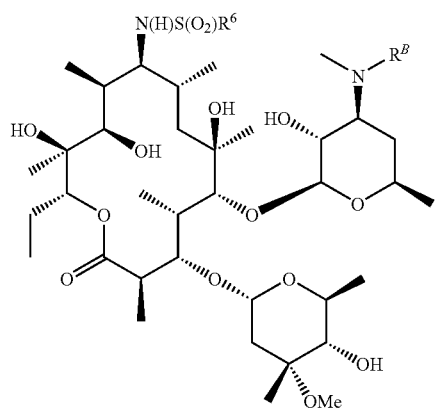 (Ig)
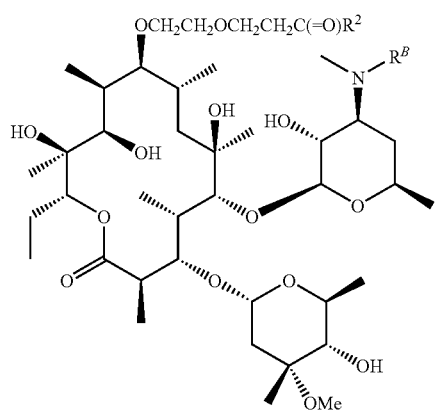 (Ih)
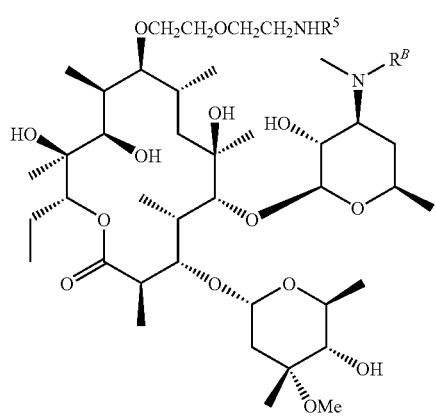 (Ii)
8. A compound according to claim 1, wherein $R^B$ is selected from the group consisting of ethyl, n-propyl, n-butyl, 2-butyl,
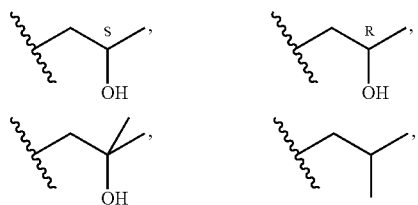
-continued
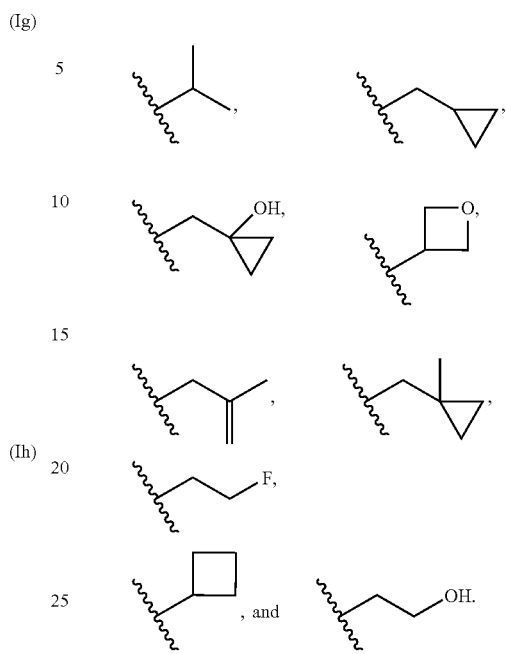
9. A compound according to claim 1, wherein $R^B$ is selected from the group consisting of
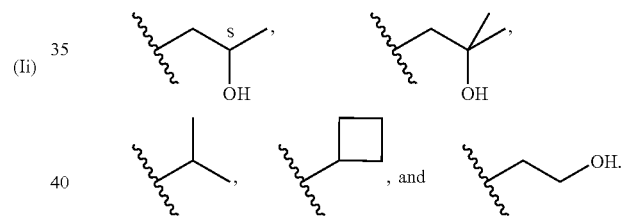
10. A compound according to claim 1, having a structure represented by formula A-12, A-13, A-15, A-21, A-71, A-74, A-77, or A-78;
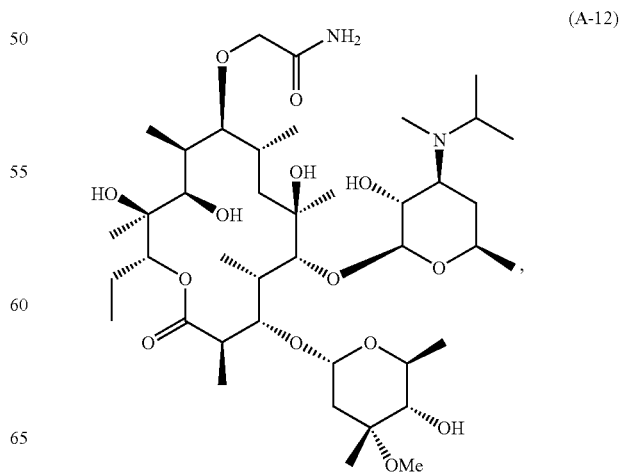
(A-12)

-continued
(A-13)
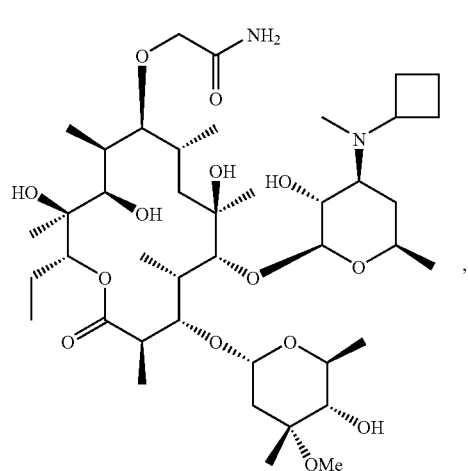
(A-15)
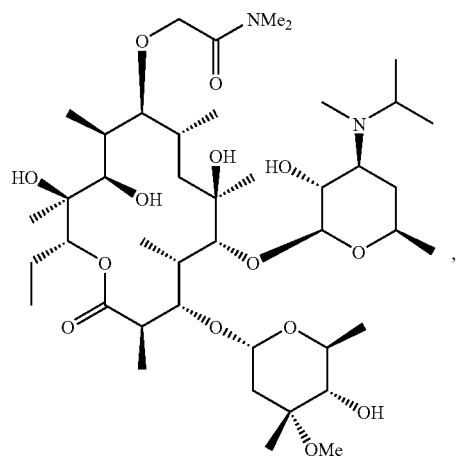
(A-21)
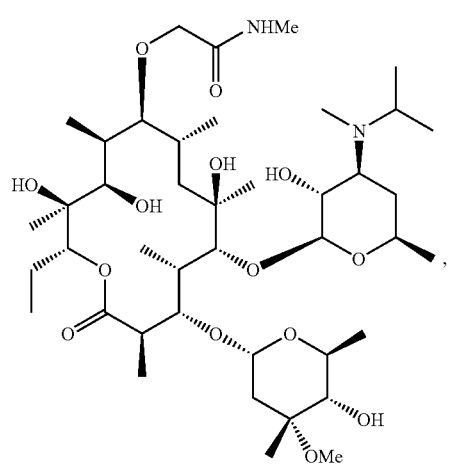
-continued
(A-71)
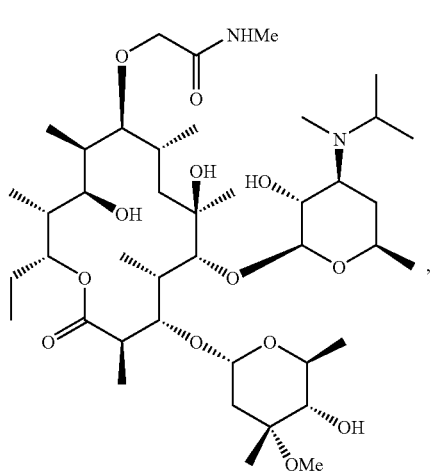
(A-74)
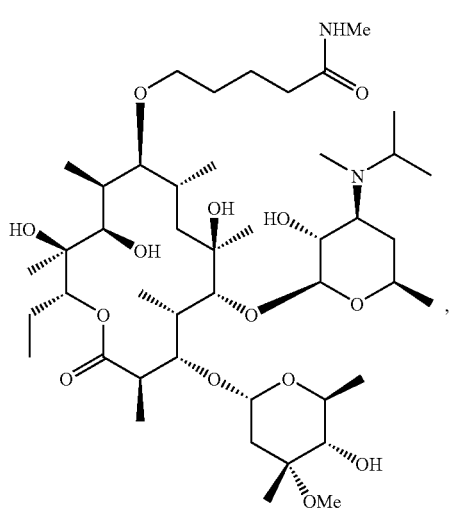
(A-77)
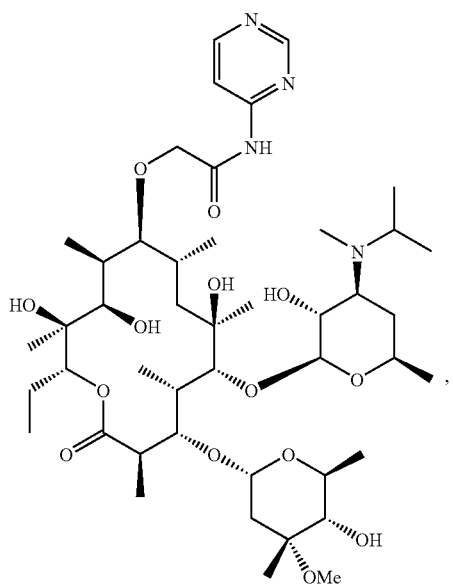

-continued

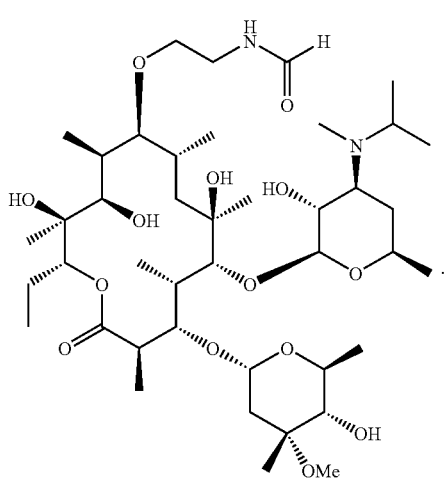

(A-78)

11. A method of treating a disease of impaired gastric motility, comprising administering to a subject in need of such treatment a therapeutically effective amount of a compound according to claim 1.

12. A method according to claim 11, wherein the disease is selected from the group consisting of gastroparesis, gastroesophageal reflux disease, anorexia, gall bladder stasis, post-operative paralytic ileus, scleroderma, intestinal pseudo-obstruction, gastritis, emesis, and chronic constipation (colonic inertia).

13. A pharmaceutical composition comprising a compound according to claim 1 and an excipient.

14. A method of inducing the contraction of a tissue contractilely responsive to motilin, which method comprises contacting such tissue with a compound according to claim 1, in an amount effective to induce such contraction.

15. A method according to claim 14, wherein the tissue is human tissue.

16. A method for preparing a medicament for treating a disease of impaired gastric motility comprising combining a compound according to claim 1 with a pharmaceutically acceptable carrier or excipient.

* * * * *

UNITED STATES PATENT AND TRADEMARK OFFICE
CERTIFICATE OF CORRECTION

| | | |
|---|---|---|
| PATENT NO. | : 7,582,611 B2 | Page 1 of 1 |
| APPLICATION NO. | : 11/416519 | |
| DATED | : September 1, 2009 | |
| INVENTOR(S) | : Liu et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 410 days Delete the phrase "by 410 days" and insert -- by 532 days --

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,582,611 B2 Page 1 of 1
APPLICATION NO. : 11/416519
DATED : September 1, 2009
INVENTOR(S) : Liu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 532 days.

Signed and Sealed this

Fourteenth Day of September, 2010

David J. Kappos
*Director of the United States Patent and Trademark Office*